US008163800B2

(12) United States Patent
Nelson et al.

(10) Patent No.: US 8,163,800 B2
(45) Date of Patent: Apr. 24, 2012

(54) PKC-ACTIVATING COMPOUNDS FOR THE TREATMENT OF NEURODEGENERATIVE DISEASES

(75) Inventors: Thomas J. Nelson, Morgantown, WV (US); Daniel L. Alkon, Bethesda, MD (US)

(73) Assignee: Blanchette Rockefeller Neurosciences Institute, Morgantown, WV (US)

( * ) Notice: Subject to any disclaimer, the term of this patent is extended or adjusted under 35 U.S.C. 154(b) by 202 days.

(21) Appl. No.: 12/510,681

(22) Filed: Jul. 28, 2009

(65) Prior Publication Data

US 2010/0022645 A1    Jan. 28, 2010

Related U.S. Application Data

(60) Provisional application No. 61/084,172, filed on Jul. 28, 2008.

(51) Int. Cl.
  *A61K 31/19* (2006.01)
  *A61K 31/20* (2006.01)
(52) U.S. Cl. ........................................ 514/557; 514/559
(58) Field of Classification Search .................. 514/557, 514/559
  See application file for complete search history.

(56) References Cited

U.S. PATENT DOCUMENTS

2005/0075393 A1    4/2005  Nishizaki

FOREIGN PATENT DOCUMENTS

JP    06279311    10/1994

OTHER PUBLICATIONS

Pub Chem Compound, May 27, 2005, XP002550143.
Fan, X., et al., Arachidonic acid and related methyl ester mediate protein kinase C activation in intact platelets through the arachidonate metabolism pathways, Biochemical and Biophysical Research Communications, Jun. 29, 1990, pp. 933-940, vol. 169, No. 3.
Invitation to Pay additional Fees dated Nov. 12, 2009.
Kanno, T, et al., "The Newly Synthesized Linoleic Acid Derivative DCP-LA Selectively Activates PKC-ε", p. 474, Dept of Physiology, Hyogo College of Med., Hyogo, Japan, 2006.
Nagata, T. et al., "FR236924, a newly synthesized derivataive of linoleic acid, ameliorates memory deficits in rats intraventricularly injected with amyloid-beta peptide." Jpn. J. Physiol. 53, Suppl. 2003: S261 No. 319.
International Search Report and Written Opinion dated Jan. 18, 2010.
Yaguchi, T. et al., "The CIS-Unsaturated Free Fatty Acid Derivative HEPBA Regulates α7 Nicotinic ACh receptor Trafficking", p. 474, Dept. of Physiology, Hyogo College of Med., Hyogo, Japan, 2006.
Kanno, T., et al., "The linoleic acid derivative DCP-LA selectively activates PKC-ε, possibly binding to the phosphatidylserine binding site", Journ. of Lipid Res., 2006, pp. 1146-1156, vol. 47, JLR Papers in Press.
Nagata, T., et al., "The newly synthesized linoleic acid derivative DCP-LA ameliorates memory deficits in animal models treated with amyloid-β peptide and scopolamine", Psychogeriatrics, 2005, pp. 122-126, vol. 5.
Ohta, K., et al., "Stearic acid facilitates hoppocampal neurotransmission by enhancing nicotinic ACh receptor responses via an PKC pathway", Molecular Brain Research, Aug. 27, 2003, pp. 83-89, vol. 119.
Tanaka, A., et al., "The Newly Synthesized Linoleic Acid Derivative FR236924 Induces a Long-Lasting Facilitation of Hippocampal Neurotransmission by Targeting Nicotinic Acetylcholine Receptors", Bioorganic & Medicinal Chem. Letters, 2003, pp. 1037-1040, vol. 13.
Yaguchi, T., et al., "Effects of cis-unsaturated free fatty acids on PKC-ε activation and nicotinic ACh receptor responses", Molecular Brain Res., 2005, pp. 320-324, vol. 133.
Yaguchi, T., et al., "Linoleic acid derivative DCP-LA improves learning impairment in SAMP8", Neuropharmacology and Neurotoxicology, Jan. 23, 2006, pp. 105-108, vol. 17, No. 1.
Yamamoto, S., et al., "The linoleic acid derivative FR236924 facilitates hippocampal synaptic transmission by enhancing activity of presynaptic α7 acetylcholine receptors on the glutamatergic terminals", Neuroscience, 2005, pp. 207-213, vol. 130.
NME Digest, Drug News Perspect, 2002, pp. 666-674, vol. 15, No. 10.

*Primary Examiner* — Sreeni Padmanabhan
(74) *Attorney, Agent, or Firm* — Finnegan, Henderson, Farabow, Garrett & Dunner, LLP

(57) ABSTRACT

The present invention relates to methods of activate an isoform of protein kinase C (PKC) for the treatment of neurological diseases including Alzheimer's disease and stroke using cyclopropanated or epoxidized derivatives of mono- and polyunsaturated fatty acids. The present invention also relates to methods of reducing neurodegeneration using cyclopropanated or epoxidized derivatives of mono- and polyunsaturated fatty acids.

15 Claims, 12 Drawing Sheets

PKC-ACTIVATING COMPOUNDS FOR THE TREATMENT OF NEURODEGENERATIVE DISEASES

This application claims the benefit of U.S. provisional patent application Ser. No. 61/084,172, filed on Jul. 28, 2008, the disclosure of which is incorporated herein by reference in its entirety.

FIELD OF THE INVENTION

The present invention relates to compositions and methods to activate an isoform of protein kinase C (PKC). The present invention also provides methods for reducing neurodegeneration and for treatment of neurological diseases including Alzheimer's disease and stroke.

BACKGROUND OF THE INVENTION

PKC Activators in Alzheimer's Disease, Stroke, and Depressive Disorders

Alzheimer's disease (AD) is a neurodegenerative disorder characterized by the progressive decline of memory and cognitive functions. Dementia associated with AD is referred to as senile dementia of the Alzheimer's type (SDAT) in usage with Alzheimer's disease. AD is characterized clinically by progressive loss of memory, cognition, reasoning, judgment, and emotional stability that gradually leads to profound mental deterioration and ultimately, death. Although there are many hypotheses for the possible mechanisms of AD, one central theory is that the excessive formation and accumulation of toxic beta-amyloid (Aβ) peptides either directly or indirectly affects a variety of cellular events and leads to neuronal damage and cell death. Selkoe, *Neuron.* 1991; 6(4): 487-98 1991; Selkoe, *J Clin Invest.* 2002; 110(10):1375-81.

AD is a progressive disorder with a mean duration of around 8-15 years between onset of clinical symptoms and death. AD is believed to represent the seventh most common medical cause of death and affects about 5 million people in the United States. The prevalence is expected to reach 7.7 million by 2030. About 1 in 8 people over the age of 65, 13% of this population, have AD (Alzheimer's Association 2008 Alzheimer's Disease Facts and Figures). AD currently affects about 15 million people world-wide (including all races and ethnic groups) and owing to the relative increase of elderly people in the population its prevalence is likely to increase over the next two to three decades. AD is at present incurable.

Protein kinase C (PKC) is one of the largest gene families of protein kinase. Several PKC isozymes are expressed in the brain, including PKC, PKCβ1, PKCβII, PKCδ, PKCε, and PKCγ. PKC is primarily a cytosolic protein, but with stimulation it translocates to the membrane. PKC has been shown to be involved in numerous biochemical processes relevant to Alzheimer's disease. PKC activation also has a crucial role in learning and memory enhancement and PKC activators have been shown to increase memory and learning. Sun and Alkon, *Eur J Pharmacol.* 2005; 512:43-51; Alkon et al., *Proc Natl Acad Sci USA,* 2005; 102:16432-16437. PKC activation also has been shown to induce synaptogenesis in rat hippocampus, suggesting the potential of PKC-mediated antiapoptosis and synaptogenesis during conditions of neurodegeneration. Sun and Alkon, *Proc Natl Acad Sci USA.* 2008; 105(36): 13620-13625. Postischemic/hypoxic treatment with bryostatin-1, a PKC activator, effectively rescued ischemia-induced deficits in synaptogenesis, neurotrophic activity, and spatial learning and memory. Sun and Alkon, *Proc Natl Acad Sci USA.* 2008. This effect is accompanied by increases in levels of synaptic proteins spiniophilin and synaptophysin and structural changes in synaptic morphology. Hongpaisan and Alkon, *Proc Natl Acad Sci USA.* 2007; 104:19571-19576. Bryostatin-induced synaptogenesis for long-term associative memory is also regulated by PKC activation. Hongpaisan and Alkon, *PNAS* 2007. PKC also activates neurotrophin production. Neurotrophins, particularly brain-derived neurotrophic factor (BDNF) and nerve growth factor (NGF), are key growth factors that initiate repair and regrowth of damaged neurons and synapses. Activation of some PKC isoforms, particularly PKCε and PKCα, protect against neurological injury, most likely by upregulating the production of neurotrophins. Weinreb et al., *FASEB Journal.* 2004; 18:1471-1473). PKC activators are also reported to induce expression of tyrosine hydroxylase and induce neuronal survival and neurite outgrowth. Du and Iacovitti, *J. Neurochem.* 1997; 68: 564-69; Hongpaisan and Alkon, PNAS 2007; Lallemend et al., J. Cell Sci. 2005; 118: 4511-25.

AD is also characterized by tau hyperphosphorylation. Tau is expressed mainly in the brain, where it regulates the orientation and stability of microtubules in neurons, astrocytes and oligodendrocytes. In AD, normal soluble tau is transformed into insoluble paired helical filaments. This is linked to the post-translational change in tau, primarily the hyperphosphorylation of tau by a number of protein kinases. Studies have shown that synthetic Aβ promotes tau phosphorylation through activation of glycogen synthase kinase-3 GSK-3. Wang et al., *Journal of Neurochemistry.* 2006; 98(4): 1167-1175. Activation of PKC has been shown to protects rat primary hippocampal neurons from Aβ-mediated neurotoxicity, through inhibition of GSK-3β. Garrido et al., *FASEB J.* 2002: 1982.

PKC also activates TNF-alpha converting enzyme (TACE, also known as ADAM17), which is an enzyme that is involved in the proteolytic conversion of membrane-bound amyloid precursor protein (APP) to its non-pathogenic soluble form, known as soluble APP-alpha or sAPPα. Alkon et al., *Trends in Pharmacological Sciences.* 2007; 28(2): 51-60; Hurtado et al., *Neuropharmacology.* 2001; 40(8): 1094-1102. These sAPPα-producing enzymes are referred to generically as alpha-secretases. Activation of TACE by PKC also reduces cellular levels of pathogenic Aβ, which is produced by cleavage of APP by the beta-secretase enzyme (BACE). This is likely due to the fact that the TACE cleavage site is within the Aβ domain of APP. Overexpression of PKCε has been shown to selectively increase the activity of endothelin-converting enzyme (ECE), which degrades Aβ. Choi et al., *Proc. Natl. Acad. Sci. USA.* 2006; 103(21): 8215-8220. In addition, subnanomolar concentrations of bryostatin and a potent synthetic analog (picolog), both PKC activators, were found to cause stimulation of non-amyloidogenic pathways by increasing TACE and thus lowering the amount of toxic Aβ produced. Khan et al., *Proc. Natl. Acad. Sci. USA.* 2009; 34(2):332-9.

Reduction of Aβ levels is a major therapeutic goal in Alzheimer's disease. It has been speculated that inhibition of Aβ formation by PKC activators may be caused by competition of TACE and BACE for their common substrate, APP.

The strategy of PKC-mediated activation of α-secretases has the advantage of three parallel beneficial consequences in AD: increasing production of sAPP-α and reducing Aβ, enhancing memory via PKC-mediated phosphorylation of downstream substrates, and decreasing phosphorylation of tau through inhibition of GSK-3β.

AD patients already have reduced levels of PKCα/ε-mediated phosphorylation of Erk½, a major downstream substrate of PKC. Khan and Alkon, *Proc Natl Acad Sci USA.* 2006; 103:13203-13207. In addition, Aβ application to normal fibroblasts reduces PKC activity because Aβ directly downregulates PKC α/ε. PKC activators, especially those specific for PKC α/ε, would counteract the effect of Aβ and thereby reverse or prevent the Aβ-induced changes.

Stroke is a leading cause of disability and death in the United States, yet limited therapeutic options exist. Several PKC isoforms have been shown to have a central role in mediating ischemic and reperfusion damage following stroke. Studies with experimental stroke models, mouse genetics, and selective peptide inhibitors and activators have demonstrated that PKCε, is involved in induction of ischemic tolerance and prevents damage, while PKCδ and γ are implicated in injury. Takayoshi et al., *Stroke*. 2007; 38(2):375-380; and Bright et al., Stroke. 2005; 36: 2781. One possible mechanisms for PKCε's protective ischemic effect is that PKCε maintaining mitochondrial function via ERK activity and by mediating adenosine-induced mitochondrial ATP-sensitive potassium channels. Another potential mechanism is that PKCε elicits a neuroprotective effect via COX-2 induction. Kim et al., *Neuroscience*. 2007; 145(3): 931-941. Prostaglandin E2 (PGE2), the product of COX-2 activity, leads to neuroprotection in cerebral ischemia. As mentioned above, postischemic/hypoxic treatment with bryostatin-1, a PKC activator, effectively rescued ischemia-induced deficits in synaptogenesis, neurotrophic activity, and spatial learning and memory. Sun and Alkon, *Proc Natl Acad Sci USA*. 2008; 105(36): 13620-13625.

Circulating Aβ protein has been shown to be elevated in patients with acute ischemic stroke Circulating Aβ1-40 level was markedly elevated in ischemic stroke patients, as compared to controls. Lee et al., *Journal of Neural Transmission*. 2005; 112(10): 1371-79. A strong positive association between progressively accumulating vascular Aβ and augmentations in arteriole and frontal cortex wall thickness AD patients also has been shown, suggesting that the continually progressing Aβ-associated angiopathy, at the arteriolar level, harms the contractile apparatus and cerebral blood flow autoregulation, thereby making the downstream capillaries vulnerable to damage. Stopa et al., *Stroke*. 2008; 39:814.

In addition, some forms of stroke are caused by Aβ, such as those associated with cerebral amyloid angiopathy, also known as congophilic amyloid angiopathy (CAA). This disorder is a form of angiopathy in which the same Aβ deposits as found in AD accumulate in the walls of the leptomeninges and superficial cerebral cortical blood vessels of the brain. Amyloid deposition predisposes these blood vessel to failure, increasing the risk of a hemorrhagic stroke. CAA is also associated with transient ischemic attacks, subarachnoid hemorrhage, Down syndrome, post irradiation necrosis, multiple sclerosis, leucoencephalopathy, spongiform encephalopathy, and dementia pugilistica.

Evidence suggests that PKCα and ε are the most important PKC isoforms in eliciting the aforementioned beneficial effects in AD, stroke, and depressive disorders. Antisense inhibition of PKCα has been shown to block secretion of sAPPα, while PKCε is the isozyme that most effectively suppresses Aβ production. Racci et al., *Mol. Psychiatry*. 2003; 8:209-216; and Zhu et al., *Biochem. Biophys. Res. Commun.* 2001; 285: 997-1006. Thus, isoform specific PKC activators are highly desirable as potential anti-Alzheimer's drugs. Specific activators are preferable to compounds such as bryostatin that show less specificity because non-specific activation of PKCδ or β could produce undesirable side effects.

Moreover, PKCε is also expressed at very low levels in all normal tissues except for brain. Mischak et al., *J. Biol. Chem.* 1993; 268: 6090-6096; Van Kolen et al., *J. Neurochem*. 2008; 104:1-13. The high abundance of PKCε in presynaptic nerve fibers suggest a role in neurite outgrowth or neurotransmitter release. Shirai et al., *FEBS J.* 2008; 275; 3988-3994). Therefore, effects of specific PKCε activators would be largely restricted to brain, and unlikely to produce unwanted peripheral side effects.

PUFAs as PKC Activators

Some PUFAs, such as arachidonic acid (see FIG. 1), have been known for many years to be natural activators of PKC. Docosahexaenoic acid (DHA) is also a known activator of PKC and has recently been shown to slow the accumulation of Aβ and tau proteins associated with the brain-clogging plaques and tangles implicated in AD. Sahlin et al., *Eur J Neurosci*. 2007; 26(4):882-9.

Kanno et al. described effect of 8-[2-(2-pentyl-cyclopropylmethyl)-cyclopropyl]-octanoic acid (DCP-LA), a newly synthesized linoleic acid derivative with cyclopropane rings instead of cis-double bonds, on protein kinase C (PKC) activity. *Journal of Lipid Research*. 2007; 47: 1146-1156. DCP-LA activated PKCε, with a greater than 7-fold potency over other PKC isozymes. This indicates that DCP-LA is highly specific for PKCε. This compound also facilitated hippocampal synaptic transmission by enhancing activity of presynaptic acetylcholine receptors on the glutamnatergic terminals or neurons. However, DCP-LA requires relatively high concentrations to produce its maximal effect.

WO 2002/50113 to Nishizaki et al., discloses carboxylic acid compounds and their corresponding salts having cyclopropane rings for LTP-like potentiation of synaptic transmission or for use as a cognition-enhancing drug or a drug to treat dementia. Their synthetic examples disclose preparation of esters but their experimental results teach the use of free acids. The reason is that the carboxylic acid group of the fatty acid starting material would react with the diethylzinc used in the Simmons-Smith reaction. The methyl ester acts as a protecting group and may be cleaved off by hydrolysis or allowed to remain as needed.

The caveats with the prior art finding include the necessity of administering high concentrations of to achieve the foregoing effects, non-specific activation of PKC isoforms, or rapid metabolism and sequestration of unmodified PUFAs into fat tissues and other organs where they are incorporated into triglycerides and chylomicrons. *J Pharmacobiodyn*. 1988; 11(4):251-61. In addition use of unmodified PUFAs would have a myriad of adverse side effects. For example, arachidonic acid is a biochemical precursor to prostaglandins, thromboxanes, and leukotrienes, which have potent pro-inflammatory effects. This would be undesirable for treatment of Alzheimer's disease where the pathology likely involves inflammation. Other essential fatty acids may also possess a multitude of other biological effects, including enhancement of nitric oxide signaling, anti-inflammatory effects, and inhibition of HMG-CoA reductase, which would interfere with cholesterol biosynthesis.

Because of the limited existing options for treating both AD and stroke, new therapeutics that can selectively activate only the PKC isoforms that elicit neuroprotection are needed.

PUFAs and MUFAs and Disease

A growing number of studies have suggested that omega-3 PUFAs can be beneficial for other mood disturbance disorders such as clinical depression, bipolar disorder, personality disorders, schizophrenia, and attention deficit disorders. Ross et al., *Lipids Health Dis*. 2007; 18;6:21. There is an abundance of evidence linking omega-3 fatty acids, particularly docosahexaenoic and eicosapentaenoic acids, and a healthy balance of omega-3 to omega-6 fatty acids, to lowering the risk of depression. Logan et al., *Lipids Health Dis*. 2004; 3:

25. Levels of omega-3 fatty acids were found to be measurably low and the ratio of omega-6 to omega-3 fatty acids were particularly high in a clinical study of patients hospitalized for depression. A recent study demonstrated that there was a selective deficit in docosahexaenoic in the orbitofrontal cortex of patients with major depressive disorder. McNamara et al. *Biol Psychiatry.* 2007; 62(1):17-24. Several studies have also shown that subjects with bipolar disorder have lower levels omega-3 fatty acids. In several recent studies, omega-3 fatty acids were shown to be more effective than placebo for depression in both adults and children with bipolar depression. Osher and Belmaker, *CNS Neurosci Ther.* 2009; 15(2): 128-33; Turnbull et al., *Arch Psychiatr Nurs.* 2008; 22(5): 305-11.

Extensive research also indicates that omega-3 fatty acids reduce inflammation and help prevent risk factors associated with chronic diseases such as heart disease, cancer, inflammatory bowel disease and rheumatoid arthritis. Calder et al., *Biofactors.* 2009; 35(3):266-72; Psota et al., *Am J Cardiol.* 2006; 98(4A):3i-18i; Wendel et al., *Anticancer Agents Med Chem.* 2009; 9(4):457-70.

Monounsaturated fatty acids also have been shown to be beneficial in disorders. There is good scientific support for MUFA diets as an alternative to low-fat diets for medical nutrition therapy in Type 2 diabetes. Ros, American *Journal of Clinical Nutrition.* 2003; 78(3): 6178-6258. High-monounsaturated fatty acid diets lower both plasma cholesterol and triacylglycerol concentrations. Kris-Etherton et al., *Am J Clin Nutr.* December 1999; 70(6):1009-15.

Figure 1:
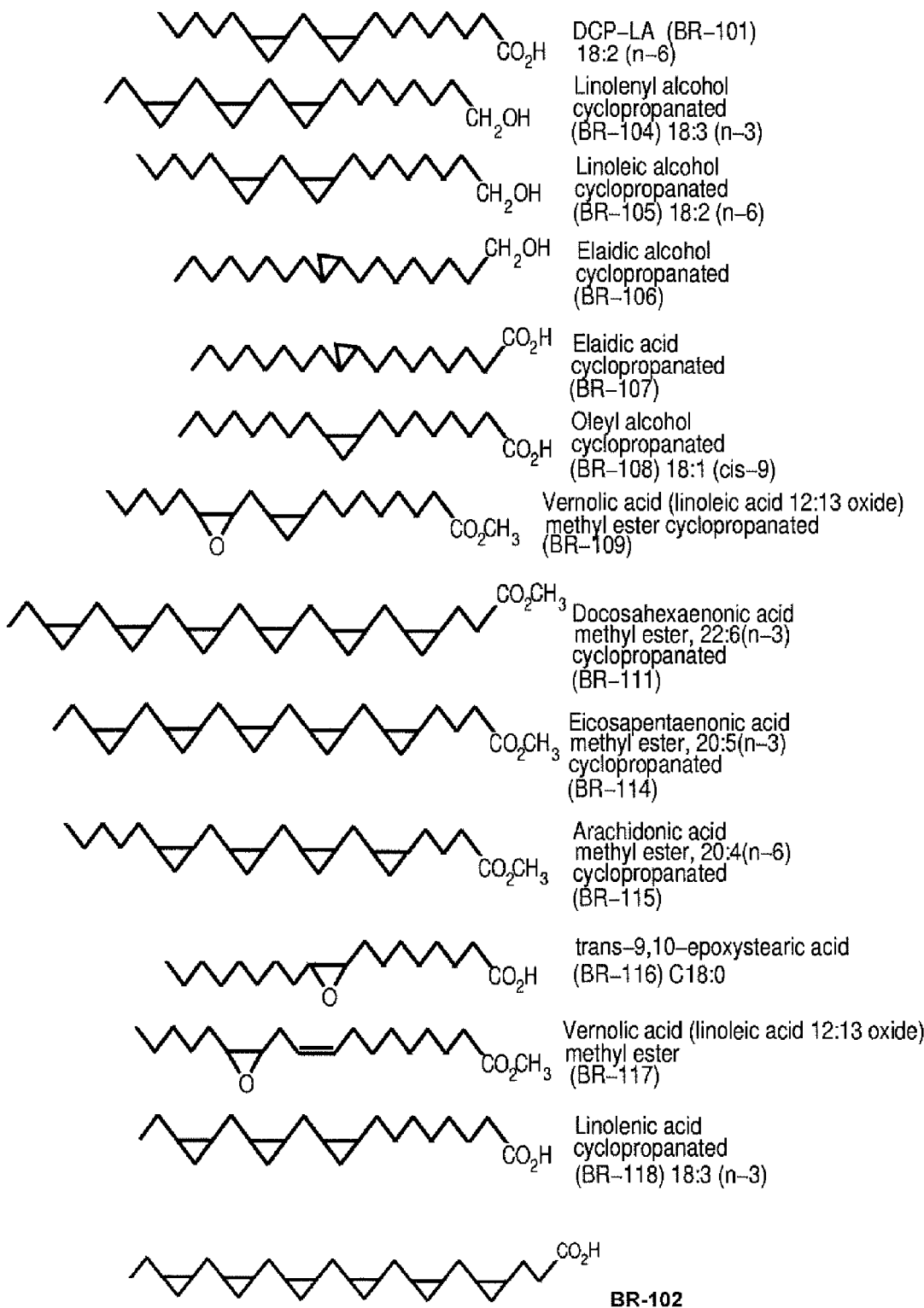
FIG. 1 Structures of and of molecules contemplated for use according to the present invention (BR-101 through BR-118).

The present invention provides a method for activating PKCε using certain derivatives of polyunsaturated fatty acids (PUFA) or monounsaturated fatty acids (MUFA). These compounds activate PKCε at nanomolar concentrations which makes them excellent candidates for the treatment of AD, stroke, and other neurological diseases in which PKCε is neuroprotective.

DEFINITIONS

A "fatty acid" is a carboxylic acid with an unbranched aliphatic chain containing from about 4 to 30 carbons; most long chain fatty acids contain between 10 and 24 carbons. Fatty acids can be saturated or unsaturated. Saturated fatty acids do not contain any double bonds or other functional groups along the chain. Unsaturated fatty acids contain one or more alkenyl functional groups, i.e., double bonds, along the chain. The term "polyunsaturated fatty acid" or "PUFA" means a fatty acid containing more than one double bond. There are three classes of PUFAs, omega-3 PUFAs, omega-6 PUFAs, and omega-9 PUFAS. In omega-3 PUFAs, the first double bond is found 3 carbons away from the last carbon in the chain (the omega carbon). In omega-6 PUFAs the first double bond is found 6 carbons away from the chain and in omega-9 PUFAs the first double bond is 9 carbons from the omega carbon.

PUFAs are also called "polyenoic fatty acids." As used herein, the term PUFA includes both naturally-occurring and synthetic fatty acids. A major source for PUFAs is from marine fish and vegetable oils derived from oil seed crops, although the PUFAs found in commercially developed plant oils are typically limited to linoleic acid and linolenic acid (18:3 delta 9,12,15).

A "cis-PUFA" is one in which the adjacent carbon atoms are on the same side of the double bond.

The abbreviation X:Y indicates an acyl group containing X carbon atoms and Y double bonds. For example, linoleic acid would be abbreviated 18:2.

A "methylene-interrupted polyene" refers to a PUFA having two or more cis double bonds separated from each other by a single methylene group.

A "non-methylene-interrupted polyene," or "polymethylene-interrupted fatty acid," refers to a PUFA having two or more cis double bonds separated by more than one methylene group.

A "monounsaturated fatty acid" (MUFA) is a fatty acid that has a single double bond in the fatty acid chain and all the remaining carbon atoms in the chain are single-bonded. Exemplary MUFAs include oleic acid, myristoleic acid and palmitoleic acid.

A "cis-monounsaturated fatty acid" means that adjacent hydrogen atoms are on the same side of the double bond.

Conjugated fatty acids such as conjugated linoleic acid (9-cis, 11-trans-octadecadienoic acid) possess a conjugated diene, that is, two double bonds on adjacent carbons. Some evidence suggests that conjugated linoleic acid has antitumor activity.

Exemplary PUFAs include lineoleic acid (9,12-octadecadienoic acid); γ-linolenic acid (GLA; 6,9,12-octadecatrienoic acid); α-linolenic acid (9,12,15-octadecatrienoic acid); arachidonic acid (5,8,11,14-eicosatetraenoic acid); eicosapentanoic acid (EPA; 5,8,11,14,17-eicosapentanoic acid); docosapentaenoic acid (DPA; 7,10,13,16,19-docosapentaenoic acid); docosahexaenoic acid (DHA; 4,7,10,13,16,19-docosahexanoic acid); and stearidonic acid (6,9,12,15-octadecatetraenoic acid).

As used herein, the term "cyclopropane" refers to a cycloalkane molecule with the molecular formula C3H6, consisting of three carbon atoms linked to each other to form a ring, with each carbon atom bearing two hydrogen atoms.

An "epoxide" refers to a cyclic ether with three ring atoms.

As used herein, a "PUFA derivative" refers to a PUFA, or alcohol or ester thereof, in which at least one of the double bonds has been cyclopropanated or epoxidized.

As used herein, a "MUFA derivative" refers to a MUFA, or alcohol or ester thereof, in which the double bond has been cyclopropanated or epoxidized.

"Selective activation" of PKCε means that the PUFA derivative compound of the present invention activates PKCε to a greater detectable extent than any other PKC isozyme. In specific embodiments, the PUFA derivative activates PKCδ at least 1-fold, 2-fold or 5-fold over the other PKC isozymes as measured using e.g., the PKC activation assay described herein. Upon activation, protein kinase C enzymes are translocated to the plasma membrane by RACK proteins (membrane-bound receptor for activated protein kinase C proteins). In general, upon activation, protein kinase C enzymes are translocated to the plasma membrane by RACK proteins. Other indicia of PKC activation include phosphorylation at specific C-terminal serine/threonine residues by phosphatidylinositol-trisphosphate-dependent kinase (PDK1), with at least two additional phosphorylations and/or autophosphorylations of well-conserved sequences in each enzyme of the PKC family. Activation of PKC is described in Sun and Alkon, *Recent Patents CNS Drug Discov.* 2006; 1(2):147-56.

"Neurodegeneration" refers to the progressive loss of structure or function of neurons, including death of neurons.

For purposes of the present invention, a "neurological disease" refers to any central nervous system (CNS) or peripheral nervous system (PNS) disease that is associated with the β-amyloidogenic processing of APP. This may result in neuronal or glial cell defects including but not limited to neuronal loss, neuronal degeneration, neuronal demyelination, gliosis (i.e., astrogliosis), or neuronal or extraneuronal accumulation of aberrant proteins or toxins (e.g., Aβ).

One exemplary neurological disease is AD. Another exemplary neurological disease is congophilic angiopathy (CAA), also referred to as cerebral amyloid angiopathy.

The term "Alzheimer's Disease" or "AD" refers to any condition where Aβ deposition will eventually in the cells of the central nervous system. In one, non-limiting embodiment, Aβ, particularly Aβ1-42, peptide is formed from the β-amyloidogenic metabolism of APP. AD may be heritable in a Familial manifestation, or may be sporadic. Herein, AD includes Familial, Sporadic, as well as intermediates and subgroups thereof based on phenotypic manifestations.

Another neurological disease is Down syndrome (DS). Subjects with DS invariably develop (in their third or fourth decade) cerebral amyloid (Aβ) plaques and neurofibrillary tangles (NFTs), the characteristic lesions of AD. Recent studies have shown that the Aβ42 is the earliest form of this protein deposited in Down syndrome brains, and may be seen in subjects as young as 12 years of age, and that soluble Aβ can be detected in the brains of DS subjects as early as 21 gestational weeks of age, well preceding the formation of Aβ plaques. Gyure et al., *Archives of Pathology and Laboratory Medicine*. 2000; 125: 489492.

As used herein, the term "subject" includes a mammal.

The phrase "pharmaceutically acceptable" refers to molecular entities and compositions that are physiologically tolerable and do not typically produce untoward reactions when administered to a subject. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "pharmaceutically acceptable carrier" means a chemical composition with which the active ingredient may be combined and which, following the combination, can be used to administer the active ingredient to a subject and can refer to a diluent, adjuvant, excipient, or vehicle with which the compound is administered.

The terms "therapeutically effective dose" and "effective amount" refer to an amount of a therapeutic agent that results in a measurable therapeutic response. A therapeutic response may be any response that a user (e.g., a clinician) will recognize as an effective response to the therapy, including improvement of symptoms and surrogate clinical markers. Thus, a therapeutic response will generally be an amelioration or inhibition of one or more symptoms of a disease or condition e.g., AD. A measurable therapeutic response also includes a finding that a symptom or disease is prevented or has a delayed onset, or is otherwise attenuated by the therapeutic agent.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The present invention includes use of cyclopropanated and epoxidized derivatives of PUFAs or MUFAs in which one, some, or all of the double bonds are replaced by a cyclopropane group or an epoxide group. The terminal function may be a free carboxylic acid, or a methyl ester, ethyl ester, or some other alkyl ester with an aliphatic or aromatic alcohol. This alcohol specifically may also include glycerol and derivatives thereof. Glycerol derivatives are biologically important because the fatty acids are most frequently found conjugated to glycerol in the form of phosphatidylcholine, phosphatidylserine, or phosphatidic acids. For example, triacylglycerols are compounds in which the carboxyl groups of fatty acids are esterified to the hydroxyls of all three carbons found in glycerol are referred to as triacylglycerols or triglycerides.

The purpose of esterifying the carboxylic acid is to facilitate transport across the blood-brain barrier by eliminating the negative charge. The purpose of an alcohol group is also to facilitate transport across the blood-brain barrier.

In one embodiment, the fatty acid which forms the basis for the compounds used in the present invention is a polyunsaturated fatty acid having the following structure:

$$CH_3(CH_2)_4(CH=CHCH_2)x(CH_2)yCOOH$$

wherein X is between 2 and 6, and Y is between 2 and 6, and include methylene- or polymethylene-interrupted polyenes. Exemplary polyunsaturated fatty acids include linoleic acid, γ-linoleic, arachidonic acid, and adrenic acid having the following structures:

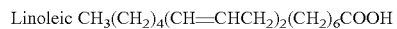

Linoleic $CH_3(CH_2)_4(CH=CHCH_2)_2(CH_2)_6COOH$

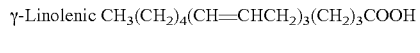

γ-Linolenic $CH_3(CH_2)_4(CH=CHCH_2)_3(CH_2)_3COOH$

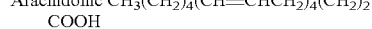

Arachidonic $CH_3(CH_2)_4(CH=CHCH_2)_4(CH_2)_2COOH$

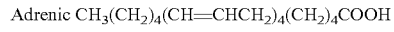

Adrenic $CH_3(CH_2)_4(CH=CHCH_2)_4(CH_2)_4COOH$

These are omega-6 PUFAs.

In another embodiment, the fatty acid which forms the basis for the compounds used in the present invention is a polyunsaturated fatty acid having the following structure:

CH$_3$CH$_2$(CH═CHCH$_2$)x(CH$_2$)yCOOH wherein X is between 2 and 6, and Y is between 2 and 6 and include methylene- or polymethylene-interrupted polyenes. Exemplary polyunsaturated fatty acids include α-lineoleic acid, docosahexaenoic acid, eicosapentaenoic acid, eicosatetraenoic acid having the following structures:

Alpha-Linolenic CH$_3$CH$_2$(CH═CHCH$_2$)$_3$(CH$_2$)$_6$COOH

Eicosatetraenoic CH$_3$CH$_2$(CH═CHCH$_2$)$_4$(CH$_2$)$_5$COOH

Eicosapentaenoic CH$_3$CH$_2$(CH═CHCH$_2$)$_5$(CH$_2$)$_2$COOH

Docosahexaenoic CH$_3$CH$_2$(CH═CHCH$_2$)$_6$(CH$_2$)$_2$COOH

These are known as omega-3 PUFAs.

In a specific embodiment, the compound of the present invention is an ester of a cis-PUFA, in which the hydroxyl group is replaced by an alkoxy group, and in which at least one of the double bonds has been cyclopropanated. The starting material for this embodiment has the following structures:

CH$_3$(CH$_2$)$_4$(CH═CHCH$_2$)x(CH$_2$)yCOOR or
CH$_3$CH$_2$(CH═CNCH$_2$)x(CH$_2$)yCOOR wherein R is the alkyl group from an alcohol including monohydric alcohols and polyhydric alcohols including but not limited to methanol, ethanol, propanol, butanol, pentanol, glycerol, mannitol, and sorbitol.

In a further embodiment, the compound contains at least three cyclopropanated double bonds.

In another embodiment, the fatty acid which forms the basis for the compounds used in the present invention is a monounsaturated fatty acid having the following structure:

CH$_3$(CH$_2$)xCH═CH(CH$_2$)yCOOH wherein X and Y are odd numbers between 3 and 11.

Exemplary monounsaturated fatty acids that can be the basis for the compounds used in the present invention include cis- and trans-monounsaturated fatty acids such as oleic acid, elaidic acid, obtusilic acid, caproleic acid, lauroleic acid, linderic acid, myristoleic acid, palmitoleic acid, vaccenic acid, gadoleic acid, erucic acid, and petroselinic acid.

An ester according to the invention, means a monoester or a polyester. Esters of fatty acids include methyl, propyl, and butyl esters, and also esters resulting from more complex alcohols such as propylene glycol. In non-limiting embodiments, R' is straight or branched and includes methyl, ethyl, propyl, isopropyl, butyl, isobutyl, secbutyl, tert-butyl, pentyl, hexyl, heptyl, octyl, nonyl, decyl, undecyl, dodecyl, tridecyl, and tetradecyl. An ester may also be formed from a fatty acid linked to a fatty alcohol in an ester linkage.

The ester can be a alcohol ester, including but not limited to an aliphatic alcohol ester. In one embodiment, the alcohol ester is a glycerol ester. Glycerol esters of fatty acids include glycerol fatty acid ester, glycerol acetic acid fatty acid ester, glycerol lactic acid fatty acid ester, glycerol citric acid fatty acid ester, glycerol succinic acid fatty acid ester, glycerol diacetyl tartaric acid fatty acid ester, glycerol acetic acid ester, polyglycerol fatty acid ester, and polyglycerol condensed ricinoleic acid ester.

In another specific embodiment, the compound is an alcohol of a cis-PUFA in which at least one of the double bonds has been cyclopropanated. In a further embodiment, the compound is an alcohol of a cis-PUFA which contains at least three cyclopropanated double bonds. These compounds include but are not limited to linoleic alcohol dicyclopropane (BR-105), or linolenic alcohol tricyclopropane (BR-104). In this embodiment, R' can be a normal or branched chain alcohol or a phenolic alcohol.

In another embodiment, the compound of the present invention, the compound is a cis-polyunsaturated fatty acid, or derivative thereof, in which at least one of the double bonds is replaced with an epoxyl group. In a further embodiment, the compound contains at least three epoxidized double bonds.

In a specific embodiment, the compound is an epoxidized ester of a cis-PUFA, including but not limited to a fatty alcohol ester. The esters can be the same esters as described above for the cyclopropanated PUFAS. In a further embodiment the alcohol can be an aliphatic alcohol ester, such as glycerol.

In another specific embodiment, the compound is an epoxidized cis-polyunsaturated fatty alcohol such as linoleic alcohol dicyclopropane or linolenic alcohol tricyclopropane. The alcohols can be the same as described above for the cyclopropanated PUFAS.

In another embodiment, the compound includes cyclopropanated or epoxidized lipids derived from cis-monounsaturated fatty acids (cis-monoenoic acids), such as oleic acid, elaidic acid, elaidic alcohol, oleyl alcohol, and 1-monolinoleyl rac-glycerol. Exemplary compounds include eliadic alcohol cyclopropane (BR-106), eliadic acid cyclopropane (BR-107), and oleyl alcohol cyclopropane (BR-108).

A further embodiment includes cyclopropanated lipids derived from cis-monounsaturated fatty acids or unsaturated fatty acids, fatty acid esters, or fatty acid alcohols, containing one or more epoxide residues, such as vernolic acid methyl ester cyclopropane (e.g., BR-109).

In specific embodiments, the PUFAs which forms the basis of the cyclopropanated compounds used in the present invention include but are not limited to arachidonic acid (AA), docosahexaenoic acid (DHA), and eicosapentaenoic acid (EPA). Exemplary compounds for use in the method of the present invention include docahexaenonic acid methyl ester hexacyclopropane (BR-111); eicosapentaenoic acid methyl ester pentacyclopropane (BR-114); and arachidonic acid methyl ester tetracyclopropane (BR-115).

In a further specific embodiment, the compound is a cyclopropanated PUFA derivative of docosahexaenoic acid having the following structure:

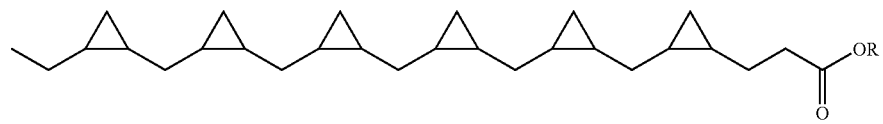

in which R is H or an alkyl group. In a specific embodiment, R is CH3 (BR-111 or DHA-CB6 methyl ester or methyl-3-(2-((2-((2-((2-((2-ethylcyclopropyl)methyl)cyclopropyl)methyl)cyclopropyl)methyl)-cyclopropyl)methyl)cyclopropyl)methyl)cyclopropyl)propanoate.

In another specific embodiment, the PUFA derivative has the following structure:

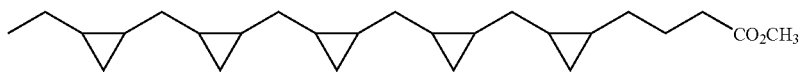

This compound is BR-114 (EPA-CP5 or methyl 4-(2((2-((2-((2-ethylcyclopropyl)methyl)cyclopropyl)methyl)cyclopropyl)methyl)cyclopropyl)methyl)-cyclopropyl)butanoate methyl ester).

In still another specific embodiment, the PUFA derivative has the following structure:

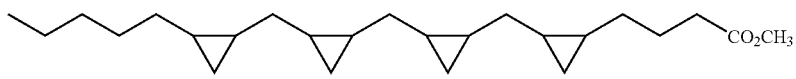

This compound is BR-115 (AA-CP4 or methyl 4-(2-((2-((2-((2-pentylcyclopropyl)methyl)cyclopropyl)methyl)cyclopropyl)methyl)cyclopropyl)butanoate methyl ester).

In yet another specific embodiment, the PUFA derivative has the following structure:

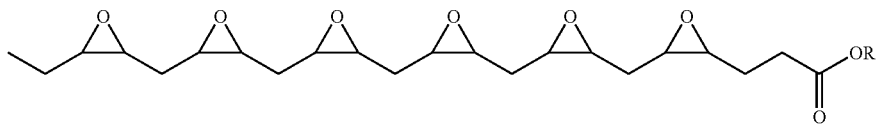

in which R is H or an alkyl ester. In a specific embodiment, R is CH3.

Naturally cyclopropanated or epoxidized MUFAS or ester or alcohol derivatives thereof contemplated for use in the present invention include malvenic acid, vernolic acid, and sterculic acid. An exemplary compound is vernolic acid methyl ester (BR-117).

Methods of Synthesis

Fatty acids, and esters and alcohols thereof, can be obtained or made from purification from natural sources, e.g., fish oil, flaxseed oil, soybeans, rapeseed oil, or algae, or synthesized using a combination of microbial enzymatic synthesis and chemical synthesis. As one example, fatty acid methyl esters can be produced by the transesterification of triglycerides of refined/edible type oils using methanol and an homogeneous alkaline catalyst.

Methods of cyclopropanation of double bonds in hydrocarbons are well known. As one example, the modified Simmons-Smith reaction is a standard method for converting double bonds to cyclopropanes. Tanaka and Nishizaki, *Bioorg. Med. Chem. Let.* 2003; 13: 1037-1040; Kawabata and Nishimura, *J. Tetrahedron.* 1967; 24: 53-58; and Denmark and Edwards, *J. Org Chem.* 1991; 56: 6974. In this reaction, treatment of alkenes with metal carbenoids, e.g., methylene iodide and diethylzinc, result in cyclopropanation of the alkene. See also, Ito et al., Organic Syntheses 1988; 6:327.

Cyclopropanation of methyl esters of was also effected using diazomethane in the presence of palladium (II) acetate as catalyst. Gangadhar et al., *Journal of the American Oil Chemists' Society.* 1988; 65(4): 601-606.

Methods of epoxidation are also well known and typically involve reaction of fatty acids dioxiranes in organic solvents. Sonnet et al., *Journal of the American Oil Chemists' Society.* 1995; 72(2):199-204. As one example, epoxidation of PUFA double bonds can be achieved using dimethyldioxirane (DMD) as the epoxidizing agent. Grabovskiy et al., *Helvetica Chimica Acta.* 2006; 89(10): 2243-53.

Methods of Treatment

The present invention contemplates treatment of neurological diseases associated with pathogenic Aβ such as AD and stroke using the PUFA derivatives disclosed herein. The present invention also contemplates prevention of neurological diseases associated with pathogenic Aβ using the PUFA derivatives disclosed herein. Without being limited to any particular mechanism, selective activation of PKCε may result in increased activation of TACE, with a concomitant decrease in production of Aβ. However, this appears to occur mainly in non-neuronal cells such as fibroblasts. Activation of PKCε may also reduce the hyperphosphorylation of the pathogenic tau protein in AD. Activation of PKCε may also induce synaptogenesis or prevent apoptosis in AD or following stroke. Activation of PKCε may also protect rat neurons from Aβ-mediated neurotoxicity through inhibition of GSK-3β. PKCε activators may also counteract the effect of Aβ on the downregulation of PKC α/ε, and thereby reverse or prevent the Aβ-induced changes. Another possible mechanism of action is the activation of Aβ-degrading enzymes such as endothelin-converting enzyme. The results of experiments presented in the Examples suggest that this may be the mechanism of action.

Yet another mechanism may be by stimulation of PKC-coupled M1 and M3 muscarinic receptors, which is reported to increase nonamyloidogenic APP processing by TACE. Rossner et al., *Prog. Neurobiol.* 1998; 56: 541-569. Muscarinic agonists rescue 3x-transgenic AD mice from cognitive deficits and reduce Aβ and tau pathologies, in part by activating the TACE/ADAM17 nonamyloidogenic pathway. Caccamo et al., *Neuron.* 2006; 49:671-682. Muscarinic receptor signaling is closely tied to PKC. Muscarinic receptor mRNA is regulated by PKC and neuronal differentiation produced by M1 muscarinic receptor activation is mediated by PKC. Barnes et al., *Life Sci.* 1997; 60:1015-1021; Vandemark et al., *J. Pharmacol. Exp. Ther.* 2009; 329(2): 532-42.

Other disorders contemplated for treatment by the methods of the present invention include, mood disorders such as depressive disorders and bipolar disorder, schizophrenia, rheumatoid arthritis, cancer, cardiovascular disease, type 2 diabetes, and any other disorder in which PUFAs or MUFAs have been shown to be beneficial, including but not limited to those mention in the background.

Formulation and Administration

The PUFA derivatives may be produced in useful dosage units for administration by any route that will permit them to cross the blood-brain barrier. It has been demonstrated PUFAs from plasma are able to cross into the brain. Rapoport et al., *J. Lipid Res.* 2001. 42: 678-685. Exemplary routes include oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration.

The compounds of the present invention can be formulated according to conventional methods. The PUFA derivative compounds can be provided to a subject in standard formulations, and may include any pharmaceutically acceptable additives, such as excipients, lubricants, diluents, flavorants, colorants, buffers, and disintegrants. Standard formulations are well known in the art. See e.g., Remington's Pharmaceutical Sciences, 20th edition, Mack Publishing Company, 2000.

In one embodiment, the compound is formulated in a solid oral dosage form. For oral administration, e.g., for PUFA, the pharmaceutical composition may take the form of a tablet or capsule prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

As one example, the drug Omacor® contains concentrated combinations of ethyl esters of an omega-3 PUFAS. Each 1-g capsule contains at least 900 mg of the ethyl esters of omega-3 fatty acids, primarily EPA (465 mg) and DHA (375 mg), according to the drug's label. Omacor® is administered up to 4 times per day as 1-gram transparent soft gelatin capsules filled with light-yellow oil. A similar composition can be used to administer the PUFA compounds of the present invention, although the present invention contemplates use of a lower dose of the PUFA derivatives. Stable wax-ester formulations of PUFAs have also been described by transesterification of stoichiometric amounts of ethyl esters enriched with n-3 PUFA and long-chain alcohols (18-22 carbon atoms) by transesterification of stoichiometric amounts of ethyl esters enriched with n-3 PUFA and long-chain alcohols (18-22 carbon atoms). Goretta et al., *Lebensmittel-Wissenschaft und-Technologie.* 2002; 35(5): 458-65.

In another embodiment, the PUFA compound is formulated for parenteral administration. The compound may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, dispersions, or emulsions in oily or aqueous vehicles, and may contain formulatory agents such as suspending, stabilizing and/or dispersing agents.

In a specific embodiment, the PUFA derivatives of the present invention are administered with a hydrophobic carrier. Hydrophobic carriers include inclusion complexes, dispersions (such as micelles, microemulsions, and emulsions), and liposomes Exemplary hydrophobic carriers are inclusion complexes, micelles, and liposomes. These formulations are known in the art (Remington's: The Science and Practice of Pharmacy 20th ed., ed. Gennaro, Lippincott: Philadelphia, Pa. 2003). The PUFA derivatives of the present invention may be incorporated into hydrophobic carriers, for example as at least 1, 5, 10, 20, 30, 40, 50, 60, 70, 80, or 90% of the total carrier by weight. In addition, other compounds may be included either in the hydrophobic carrier or the solution, e.g., to stabilize the formulation.

In addition to the formulations described previously, the PUFA derivative may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In another embodiment, the PUFA derivative can be delivered in a vesicle, particularly a micelle, liposome or an artificial LDL particle as described in U.S. patent application Ser. No. 11/648,808 to Alkon et al.

The doses for administration may suitably be prepared so as to deliver from 1 mg to 10 g, preferably from 10 mg to 1 g and very preferably from 250 mg to 500 mg of the compound per day. When prepared for topical administration or parenteral formulations they may be made in formulae containing from 0.01% to 60% by weight of the final formulation, preferably from 0.1% to 30% by weight, and very preferably from 1% to 10% by weight. The optimal daily dose will be determined by methods known in the art and will be influenced by factors such as the age of the patient and other clinically relevant factors.

Combination Drug Therapy

The PUFA compound can be used to treat patients with AD or other neurological disorders associated with Aβ in combination with other drugs that are also used to treat the disorder. Exemplary non-limiting pharmacological agents approved in the United States for the treatment of AD include cholinesterase inhibitors such as Aricept® (donepezil), Exelon® (rivastigmine), Reminyl® (galantamine), and NMDA receptor antagonists such as Namenda® (memantine). Other potential therapeutic agents include protease inhibitors (see e.g., U.S. Pat. Nos. 5,863,902; 5,872,101; inhibitors of Aβ production such as described in U.S. Pat. Nos. 7,011,901; 6,495,540; 6,610,734; 6,632,812; 6,713,476; and 6,737,420; modulators of Aβ aggregation, described in U.S. Pat. Nos. 6,303,567; 6,689,752; and inhibitors of BACE such as disclosed in U.S. Pat. Nos. 6,982,264; 7,034,182; 7,030,239. Exemplary drugs used for the treatment of stroke include aspirin, anti-platelet medications such as tissue plasminogen activator or other anticoagulants.

In a particular embodiment, the present invention contemplates combination therapy with other PKC activators, including but not limited to benzolactam macrocyclic lactones. Bryostatin-1 is a macrocyclic lactone that has been shown to modulate PKC and result in an increase in cleavage of APP by TACE into the non-amyloidogenic pathway. Bryostatin was able to increase the duration of memory retention of the marine slug *Hermissenda crassicornis* by over 500%, and was able to dramatically increase the rate of learning in rats. See U.S. patent application Ser. No. 10/919,110; Kurzirian et al., *Biological Bulletin*. 2006; 210(3): 201-14; Sun and Alkon, *European Journal of Pharmacology*. 2005; 512(1): 43-51. Other non-limiting PKC activators are described in pending U.S. patent application Ser. No. 12/068,742 to Alkon et al.

Combinations with drugs that indirectly increase TACE, such as by inhibiting endogenous TACE inhibitors or by increasing endogenous TACE activators. An alternative approach to activating PKC directly is to increase the levels of the endogenous activator, diacylglycerol. Diacylglycerol kinase inhibitors such as 6-(2-(4-[(4-fluorophenyl)phenylmethylene]-1-piperidinyl)ethyl)-7-methyl-5H-thiazolo[3,2-a]pyrimidin-5-one (R59022) and [3-[2-[4-(bis-(4-fluorophenyl)methylene]piperidin-1-yl)ethyl]-2,3-dihydro-2-thioxo-4(1H)-quinazolinone (R59949) enhance the levels of the endogenous ligand diacylglycerol, thereby producing activation of PKC. Meinhardt et al. (2002) *Anti-Cancer Drugs* 13: 725.

Still another embodiment is combination therapy with BACE inhibitors. BACE inhibitors are known and include CTS-21166, owned by CoMentis Inc., which has shown positive results in a human clinical trial. Other BACE inhibitors are described in published International PCT application WO2007/019080 and in Baxter et al., *Med. Chem.* 2007; 50(18): 4261-4264.

Compounds used in combination therapy can be administered in the same formulation as the PUFA compound of the present invention, where compatible, or can be administered in separate formulations.

Evaluation of Treatment

Evaluation of treatment with the PUFA derivatives of the present invention can be made by evaluation improvement in symptoms or clinical surrogate markers of the disease. For example, improvement in memory or cognitive skills in a treated AD subject may suggest that there is a reduction of pathogenic Aβ accumulation. Examples of cognitive phenotypes include, but are not limited to, amnesia, aphasia, apraxia and agnosia. Examples of psychiatric symptoms include, but are not limited to, personality changes, depression, hallucinations and delusions. As one non-limiting example, the Diagnostic and Statistical Manual of Mental disorders, 4th Edition (DSM-IV-TR) (published by the American Psychiatric Association) contains criteria for dementia of the Alzheimer's type.

Phenotypic manifestations of AD may also be physical, such as by the direct (imaging) or indirect (biochemical) detection of Aβ plaques. In vivo imaging of Aβ can be achieved using radioiodinated flavone derivatives as imaging agents (Ono et al., *J Med Chem.* 2005; 48(23):7253-60) and with amyloid binding dyes such as putrescine conjugated to a 40-residue radioiodinated A peptide (yielding 125I-PUT-A 1-40), which was shown to cross the blood-brain barrier and bind to Aβ plaques. Wengenack et al., *Nature Biotechnology*. 2000; 18(8): 868-72. Imaging of Aβ also was shown using stilbene [11C]SB-13 and the benzothiazole [11C]6-OH-BTA-1 (also known as [11C]PIB). Verhoeff et al., *Am J Geriatr Psychiatry*. 2004; 12:584-595.

Quantitation of Aβ (1-40) in the peripheral blood has been demonstrated using high-performance liquid chromatography coupled with tandem mass spectrometry in a linear ion trap. Du et al., *J Biomol Tech.* 2005; 16(4);356-63. Detection of single Aβ protein aggregates in the cerebrospinal fluid of Alzheimer's patients by fluorescence correlation spectroscopy also has been described. Pitschke et al., *Nature Medicine*. 1998; 4: 832-834. U.S. Pat. No. 5,593,846 describes a method for detecting soluble Aβ. Indirect detection of Aβ peptide and receptor for advanced glycation end products (RAGE) using antibodies also has been described. Lastly, biochemical detection of increased BACE-1 activity in cerebrospinal fluid using chromogenic substrates also has been postulated as diagnostic or prognostic indicator of AD. Verheijen et al., *Clin Chem.* 2006; 52:1168-1174.

Current measures for evaluation AD include observation of a clinical core of early, progressive and significant episodic memory loss plus one or more abnormal biomarkers (biological indicators) characteristic of AD, including atrophy (wasting) of the temporal lobe as shown on MRI; abnormal Aβ protein concentrations in the cerebrospinal fluid; a specific pattern showing reduced glucose metabolism on PET scans of the brain; and a genetic mutation associated with within the immediate family.

EXAMPLES

Example 1

Synthesis of Fatty Acid Methyl Esters Cyclopropanated Fatty Acid Methyl Esters

Synthesis of cyclopropanated fatty acids. Methyl esters of polyunsaturated fatty acids were cyclopropanated using the modified Simmons-Smith reaction using chloroiodomethane and diethylzinc (Tanaka et al., *Bioorg. Med. Chem. Let.* 2003; 13: 1037-40; Furukawa et al., *Tetrahedron*. 1967; 53-58; Denmark et al., *J. Org. Chem.* 1991; 56: 6974-81). All apparatus was baked at 60° C. for 1 hr and dried using a flame with dry nitrogen. A 100 ml 3-neck round bottom flask with a stirring bar and a temperature probe was surrounded by an ice-dry ice mixture and filled with 1.25 g (4.24 mmol) linoleic acid methyl ester or docosahexaenoic acid methyl ester in 25 ml dichloromethane and bubbled with $N_2$. A 1M solution of diethylzinc (51 ml, 54.94 mmol) in hexane was added anaerobically using a 24-inch-long 20-gauge needle and the solution was cooled to −5° C. Diiodomethane (8.2 ml, 101.88 mmol) or chloroiodomethane (ClCH2 I) was added dropwise, one drop per second, with constant stirring. The rate of addition was decreased if necessary to maintain the reaction mixture below 2° C. The reaction mixture became cloudy during the reaction and an insoluble white zinc product was liberated. The flask was sealed and the mixture was allowed to react for 1 hr and then allowed to come to room temperature gradually over 2 hr.

To prevent the formation of an explosive residue in the hood, diethylzinc was not evaporated off. The mixture was slowly poured into 100 ml of water under stirring to decompose any excess diethylzinc. Ethane was evolved. The mixture was centrifuged at 5000 rpm in glass centrifuge tubes and the upper aqueous layer discarded. The white precipitate was extracted with $CH_2Cl_2$ and combined with the organic phase. The organic phase was washed with water and centrifuged. The product was analyzed by silica gel G TLC using hexane plus 1% ethyl acetate and purified by chromatography on silica gel using increasing concentrations of 1-10% ethyl acetate in n-hexane and evaporated under nitrogen, leaving the methyl ester as a colorless oil.

The Simmons-Smith reaction preserves the stereochemistry of the starting materials. Furukawa et al., *Tetrahedron*. 1967; 53-58. Docosahexaenoic acid methyl ester was converted into DHA-CP6 in 90-95% yield. The product was a colorless oil with a single absorbance maximum at 202 nm in ethanol and no reaction with $I_2$. The IR spectrum showed cyclopropane ring absorption at 3070 and 1450 $cm^{-1}$. Under the same conditions, eicosapentaenoic acid methyl ester was converted to EPA-CP5, and arachidonic acid methyl ester was converted to AA-CP4. Linoleic acid methyl ester was converted to DCP-LA methyl ester which was identical to a known sample.

Hydrolysis of methyl ester. The methyl ester (0.15 g) was dissolved in 1 ml 1N LiOH and 1 ml dioxane. Dioxane and methanol were added until it became homogeneous and the solution was stirred 60° overnight. The product was extracted in $CH_2Cl_2$ and centrifuged. The aqueous layer and white interface were re-extracted with water and washed until the white layer no longer formed. The product was evaporated under $N_2$ and purified by chromatography on silica gel. The product, a colorless oil, eluted in 20% EtOAc in n-hexane. Its purity was checked by TLC in 10% EtOAc/hexane and by C18 RP-HPLC using UV detection at 205 nm.

The epoxide groups can be introduced by conventional means, e.g., by oxidation of the appropriate alkene with m-chloroperbenzoic acid or t-butylhydroperoxide.

Other compounds synthesized include those depicted in FIG. 1 (BR-101 through BR-118).

Example 2

Activation of Purified PKC Epsilon using Docosahaexanoic Acid

Protein kinase C assay. Recombinant PKC (1 ng of alpha or epsilon isoform) was mixed with the BR-101 (DCP-LA) in the presence of 10 micromolar histones, 5 mM $CaCl_2$, 1.2 µg/µl phosphatidyl-L-serine, 0.18 µg/µl 1,2-dioctanoyl-sn-glycerol (DAG), 10 mM $MgCl_2$, 20 mM HEPES (pH 7.4), 0.8 mM EDTA, 4 mM EGTA, 4% glycerol, 8 µg/ml aprotinin, 8 µg/ml leupeptin, and 2 mM benzamidine. 0.5 micro Ci [$\gamma^{32}P$] ATP was added. The incubation mixture was incubated for 15 min at 37 degrees in a total volume of 10 microliters. The reaction was stopped by spotting the reaction mixtures on 1×2 cm strips of cellulose phosphate paper (Whatman P81) and immediately washing twice for 1 hr in 0.5% $H_3PO_4$. The cellulose phosphate strips were counted in a scintillation counter. In some experiments, phosphatidylserine, diacylglycerol, and/or calcium were removed.

DHA methyl ester was purchased from Cayman Chemical (Ann Arbor, Mich.). PKC isozymes were from Calbiochem (San Diego, Calif.). Purified PKCε was purchased from Calbiochem.

Results

Figure 2:
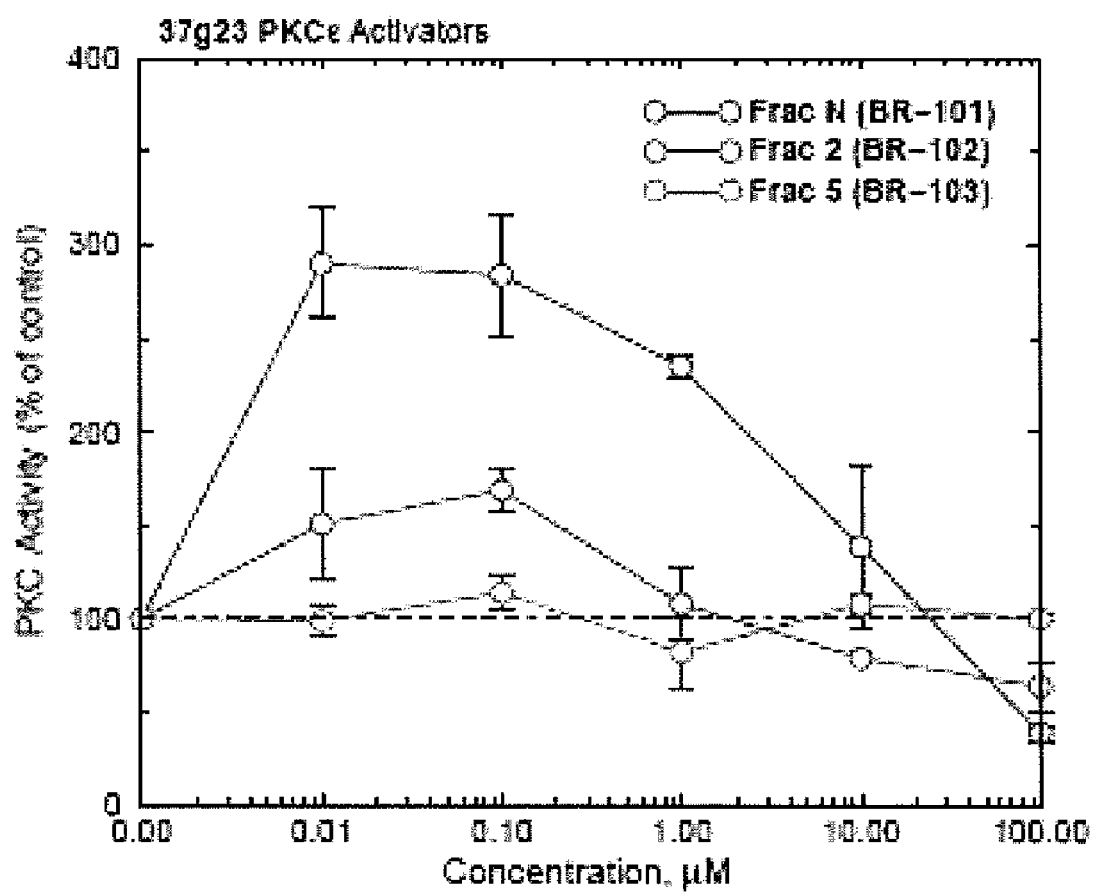
FIG. 2 shows the results of an in vitro PKCε activation by BR-101 (DCP-LA) and two less active derivatives, BR-102 and BR-103.

PKC measurements using purified PKCε showed that, at the lowest concentration tested (10 nM), compound BR-101 produced a 2.75-fold activation of PKCε (FIG. 2). PKCα was not affected (data not shown). Compound BR-102 also selectively elicited activation of PKCε to about 1.75 fold over unactivated PKCε. The effectiveness of these compounds in activating PKCε at low concentrations suggests that they will be good therapeutic candidates.

Example 3

Activation of Purified or Cellular PKC Epsilon using Other PKC Activators

Materials. Culture media were obtained from K-D Medical (Columbia, Md.) or Invitrogen (Carlsbad, Calif.). Aβ1-42 was purchased from Anaspec (San Jose, Calif.). Polyunsaturated fatty acid methyl esters were obtained from Cayman Chemicals, Ann Arbor, Mich. Other chemicals were obtained from Sigma-Aldrich Chemical Co. (St. Louis, Mo.). PKC isozymes were from Calbiochem (San Diego, Calif.). Purified PKCε was purchased from Calbiochem.

Cell culture. Rat hippocampal H19-7/IGF-IR cells (ATCC, Manassas, Va.) were plated onto poly-L-lysine coated plates and grown at 35° C. in DMEM/10% FCS for several days until about 50% coverage was obtained. The cells were then induced to differentiate into a neuronal phenotype by replacing the medium with 5 ml $N_2$ medium containing 10 ng/ml basic fibroblast growth factor at 39° C. and grown in T-75 flasks at 37° C. Human SH-SY5Y neuroblastoma cells (ATCC) were cultured in 45% F12K/45% MEM/10% FCS. Mouse N2A neuroblastoma cells were cultured in DMEM/10% FCS without glutamine. Rat hippocampal neurons from 18-day-old embryonic Sprague Dawley rat brains were plated on 12- or 96-well plates coated with poly-D-lysine (Sigma-Aldrich, St. Louis, Mo.) in B-27 neurobasal medium containing 0.5 mM glutamine and 25 µM glutamate (Invitrogen, Carlsbad, Calif.) and cultured for three days in the medium without glutamate. The neuronal cells were grown under 5% $CO_2$ in an incubator maintained at 37° C. for 14 days.

All experiments on cultured cells were carried out in triplicate unless otherwise stated. All data points are displayed as mean±SE. BR-101 (DCP-LA) was used as its free acid in all experiments, while BR-111 (DHA-CP6), BR-114 (EPA-CP5), and BR-116 (AA-CP4) were used as their methyl esters.

Protein kinase C assay. Rat hippocampal cells were cultured and scraped in 0.2 ml homogenization buffer (20 mM Tris-HCl, pH 7.4, 50 mM NaF, 1 µg/ml leupeptin, and 0.1 mM PMSF) and homogenized by sonication in a Marsonix microprobe sonicator (5 sec, 10 W). To measure PKC, 10 µl of cell homogenate or purified PKC isozyme (purchased from Calbiochem) was incubated for 15 min at 37° C. in the presence of 10 µM histones, 4.89 mM $CaCl_2$, 1.2 µg/µl phosphatidyl-L-serine, 0.18 µg/µl 1,2-dioctanoyl-sn-glycerol, 10 mM $MgCl_2$, 20 mM HEPES (pH 7.4), 0.8 mM EDTA, 4 mM EGTA, 4% glycerol, 8 µg/ml aprotinin, 8 µg/ml leupeptin, and 2 mM benzamidine. 0.5 µCi [$\gamma^{32}$P]ATP was added and $^{32}$P-phosphoprotein formation was measured by adsorption onto phosphocellulose as described previously. Nelson and Alkon, *J. Neurochemistry.* 1995; 65: 2350-57. For measurements of activation by BR-101 (DCP-LA) and similar compounds, PKC activity was measured in the absence of diacylglycerol and phosphatidylserine, as described by Kanno et al., and PKC δ, ε, η, and µ were measured in the absence of added EGTA and CaCl2, as described by Kanno et al., *J. Lipid Res.* 2006; 47: 1146-50. Low concentrations of $Ca^{2+}$ are used because high $Ca^{2+}$ interacts with the PKC phosphatidylserine binding site and prevents activation. For measurements of bryostatin activation, 1,2-diacylglycerol was omitted unless otherwise stated.

Results and Discussion

To determine their PKC isozyme specificity, the new compounds were preincubated with purified PKC for five minutes and the PKC activity was measured radiometrically. As shown for Example, 2, above, BR-101 (DCP-LA) was an effective activator of PKCε at 10 µM but had relatively small effects on the other PKC isoforms (data not shown). At higher concentrations BR-101 (DCP-LA) partially inhibited PKCδ (about 1-100 µM) and activated PKCγ(50-100 µM) (data not shown).

Figure 3:
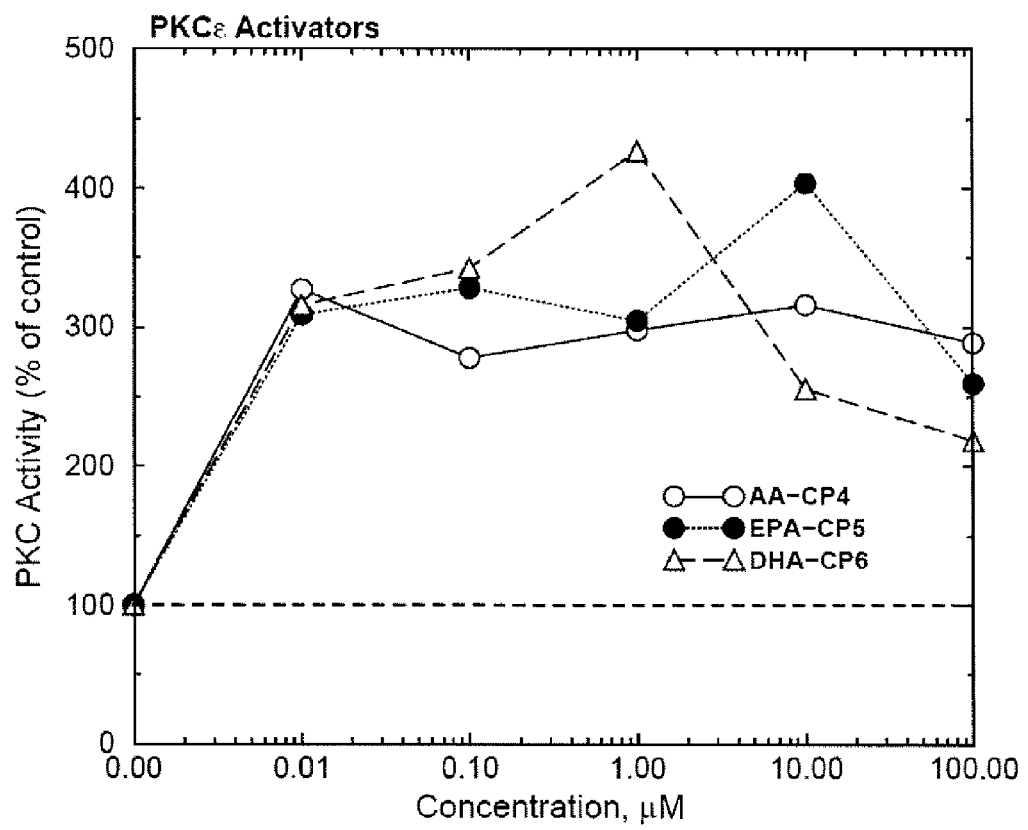
FIG. 3 shows activation of PKCε with various concentrations of BR-111 (DHA-CP6 methyl ester); BR-114 (EPA-CP5 methyl ester); and BR-115 (AA-CP4 methyl ester).
Figure 4:
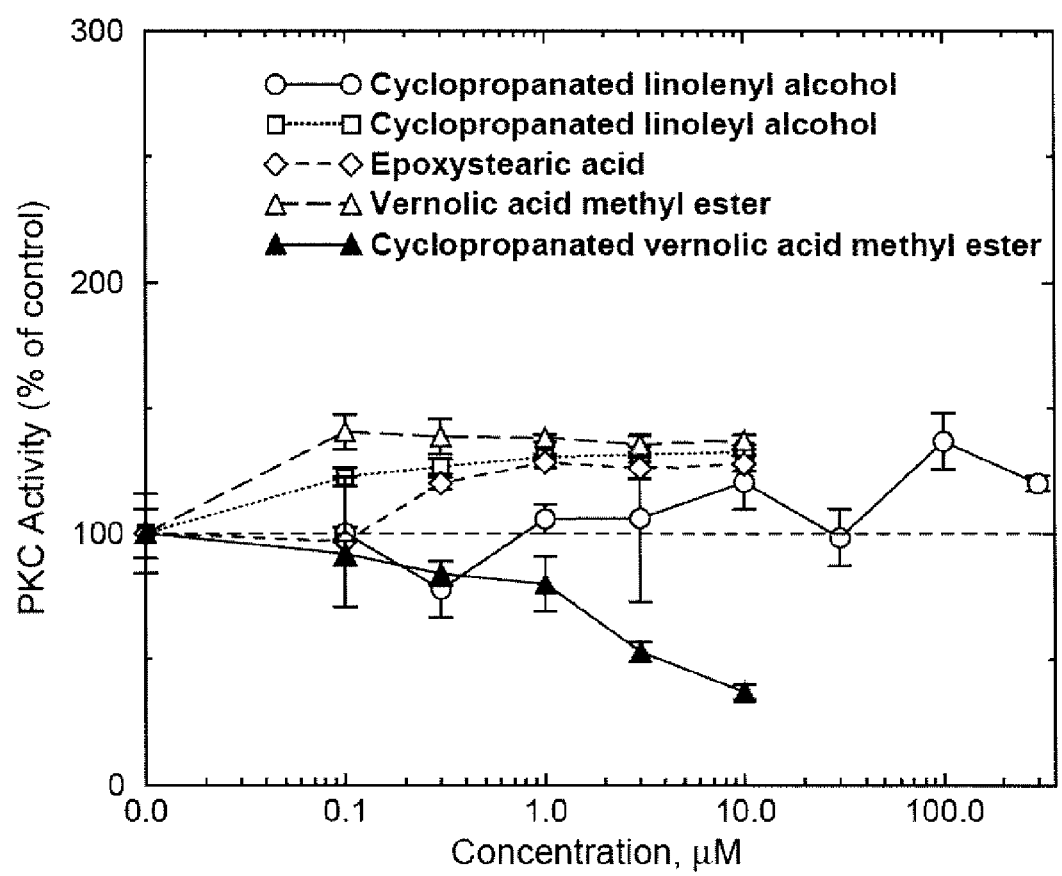
FIG. 4 shows activation of PKCε with various concentrations of other cyclopropanated and epoxidized fatty acid methyl esters: cyclopropanated linolenyl alcohol (BR-104); cyclopropanated linoleyl alcohol (BR-105); epoxystearic acid (BR-116); vernolic acid methyl ester (BR-117); and cyclopropanated vernolic acid methyl ester (BR-109).

BR-111 (DHA-CP6), BR-114 (EPA-CP5), and BR-115 (AA-CP4), which are cyclopropanated derivatives of docosahexaenoic acid, eicosapentaenoic acid, and arachidonic acid, respectively, activated purified PKCε to a similar extent (FIG. 3) The concentration needed to activate PKC was approx. 100 times lower than for BR-101 (DCP-LA), suggesting higher affinity. Cyclopropanated linolenyl and linoleyl alcohols (BR-104 and BR-105), epoxystearic acid (BR-116), and vernolic acid methyl ester (BR-117) had little or no effect on PKC (FIG. 4). Cyclopropanated vernolic acid methyl ester (BR-109) inhibited PKCε at concentrations above 1 µM (FIG. 4).

Figure 5:
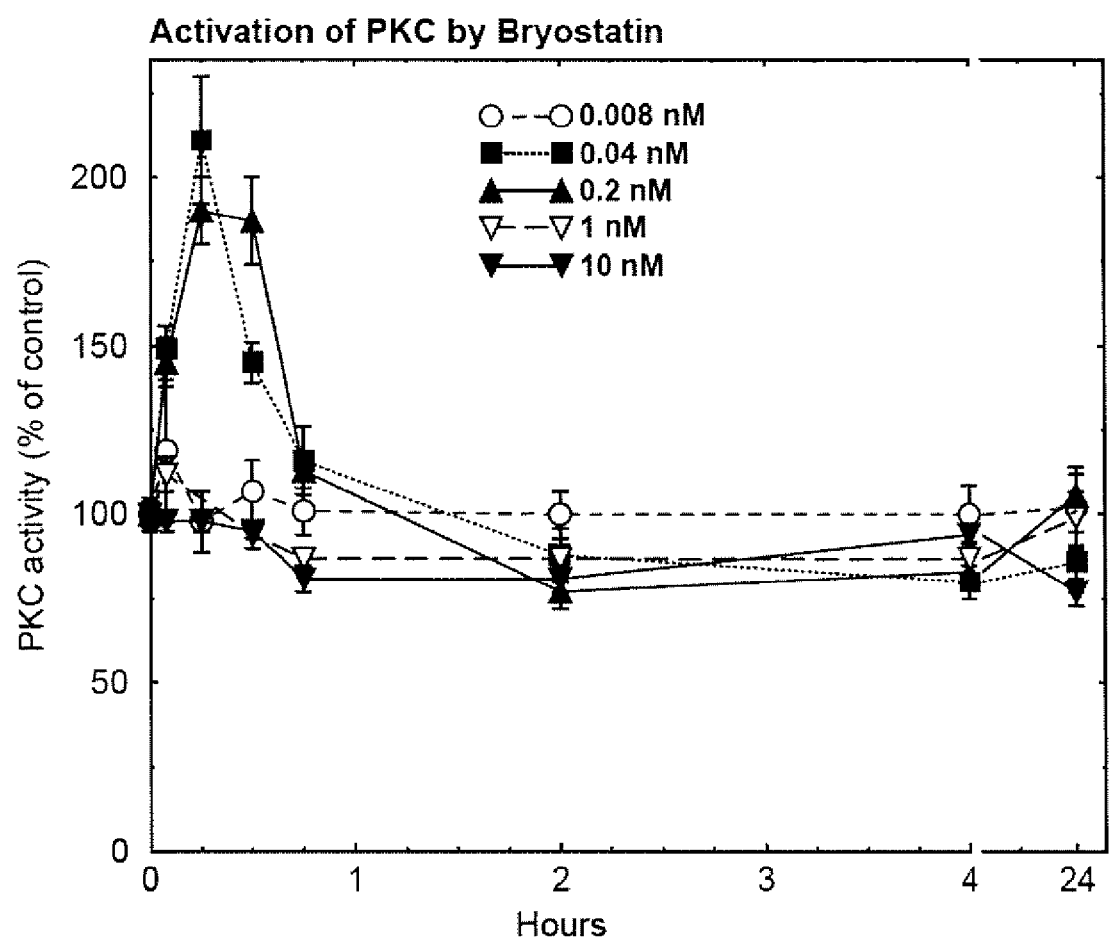
FIG. 5 shows a time course of PKC activation by various concentrations of bryostatin in H19-7/IGF-IR rat hippocampal neurons.
Figure 6:
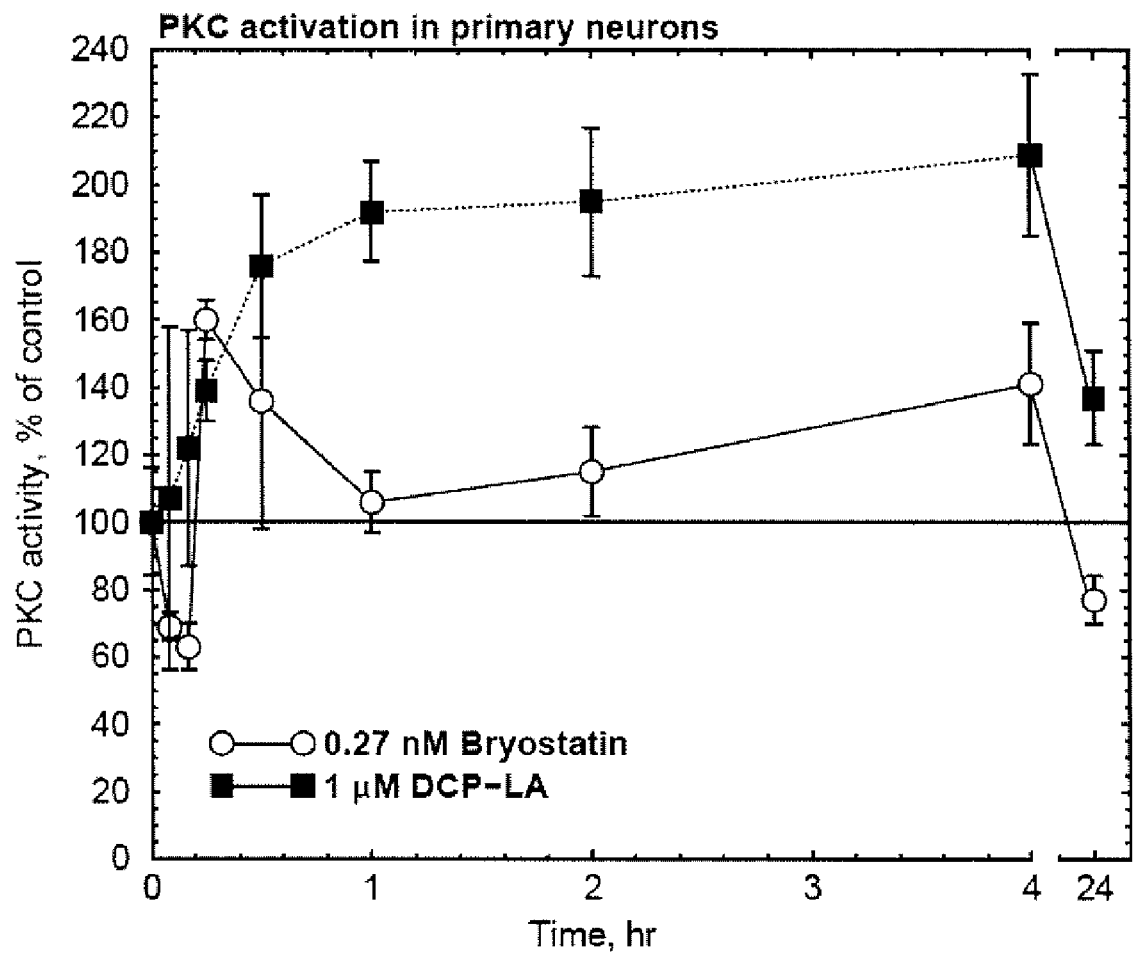
FIG. 6 shows a time course of PKC activation in rat hippocampal primary neurons by bryostatin and DCP-LA.

PKC activators that bind to the diacylglycerol binding site, including bryostatin, gnidimacrin, and phorbol esters, produce a transient activation of PKC activity, followed by a prolonged downregulation. Nelson et al., *Trends in Biochem. Sci.* 2009; 34: 136-45. This was confirmed in cultured rat hippocampal cells. Incubation of rat H19-7/IGF-IR cells with (0.04 nM and 0.2 nM) bryostatin produced a 2-fold activation that lasted 30 min, followed by a 20% downregulation that returned to baseline by 24 h (data not shown). In contrast, PKC exposed to DCP-LA remained elevated for at least four hours (FIG. 5). This sustained activation was only observed in primary neurons.

Even though bryostatin has a higher affinity for PKC than phorbol 12-myristate 13-acetate (PMA)(EC50=1.35 nM vs. 10 nM), bryostatin was much less effective than PMA at downregulating PKC. PKC activity is strongly downregulated by phorbol ester at 8 h, while PKC in bryostatin-treated cells is at or near the baseline (data not shown). This difference may explain the increases in Aβ produced by PdBu reported by da Cruz e Silva et al. *J. Neurochem.* 2009: 108: 319-30. These investigators applied 1 µM PdBu to cultured COS cells for 8 h and observed an increase in Aβ. This increase was attributed to downregulation of PKC by the phorbol ester, which is consistent with these results. Downregulation could not be measured for DCP-LA and related compounds.

Example 4

Effects of PKC Activators on Aβ Production and Degradation

Cell culture. Cell culture was performed as described above for Example 3.

Aβ Measurement and Cell Viability Assay. Aβ was measured using an Aβ 1-42 human fluorimetric ELISA kit (Invitrogen) according to the manufacturer's instructions. Results were measured in a Biotek Synergy HT microplate reader. AlamarBlue and CyQuant NF (Invitrogen) according to the manufacturer's instructions.

Results and Discussion

Figure 7A:
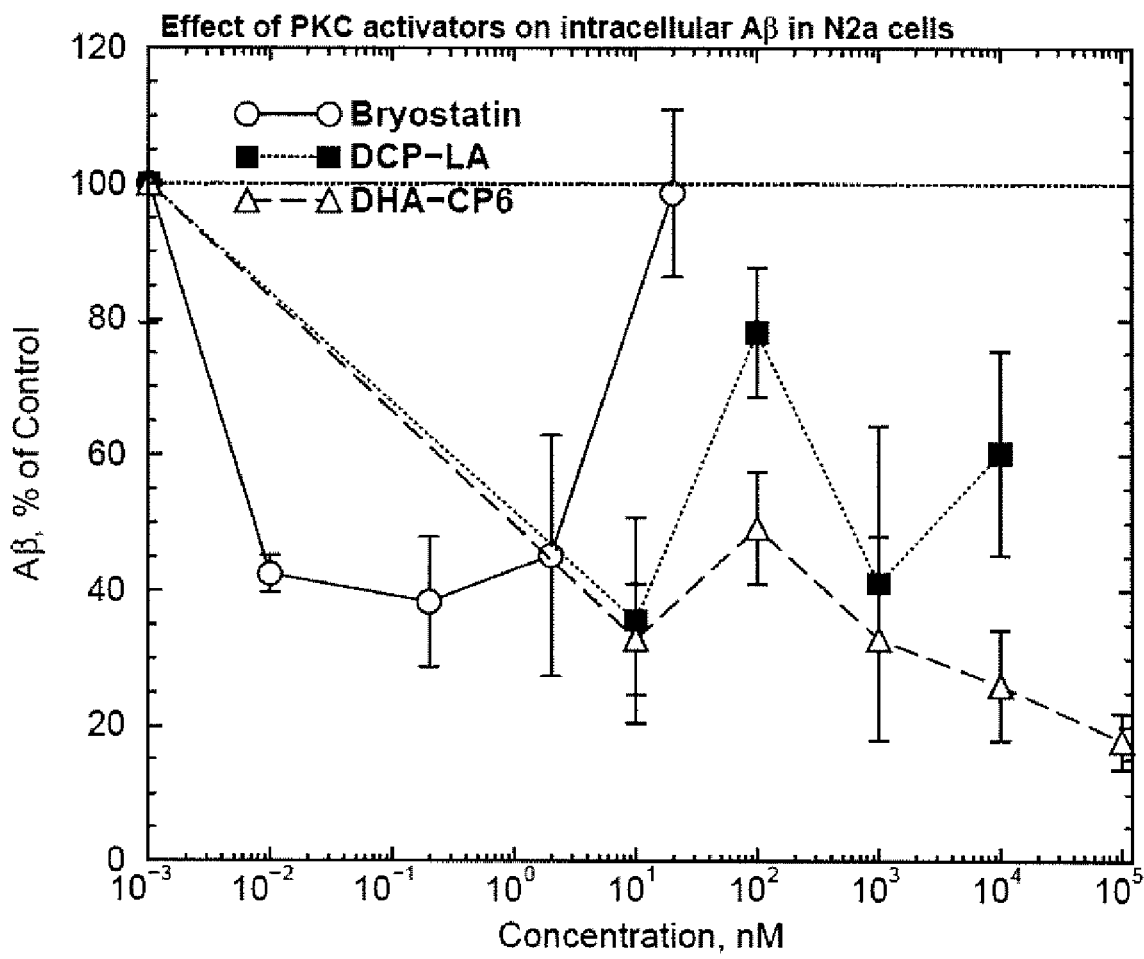
FIGS. 7a and b depict decreased levels of intracellular (7a) or secreted (7b) Aβ in neuro2a (N2A) cells exposed to PKC activators bryostatin, BR-101 (DCP-LA), or BR-111 (DHA-CP6).
Figure 7B:
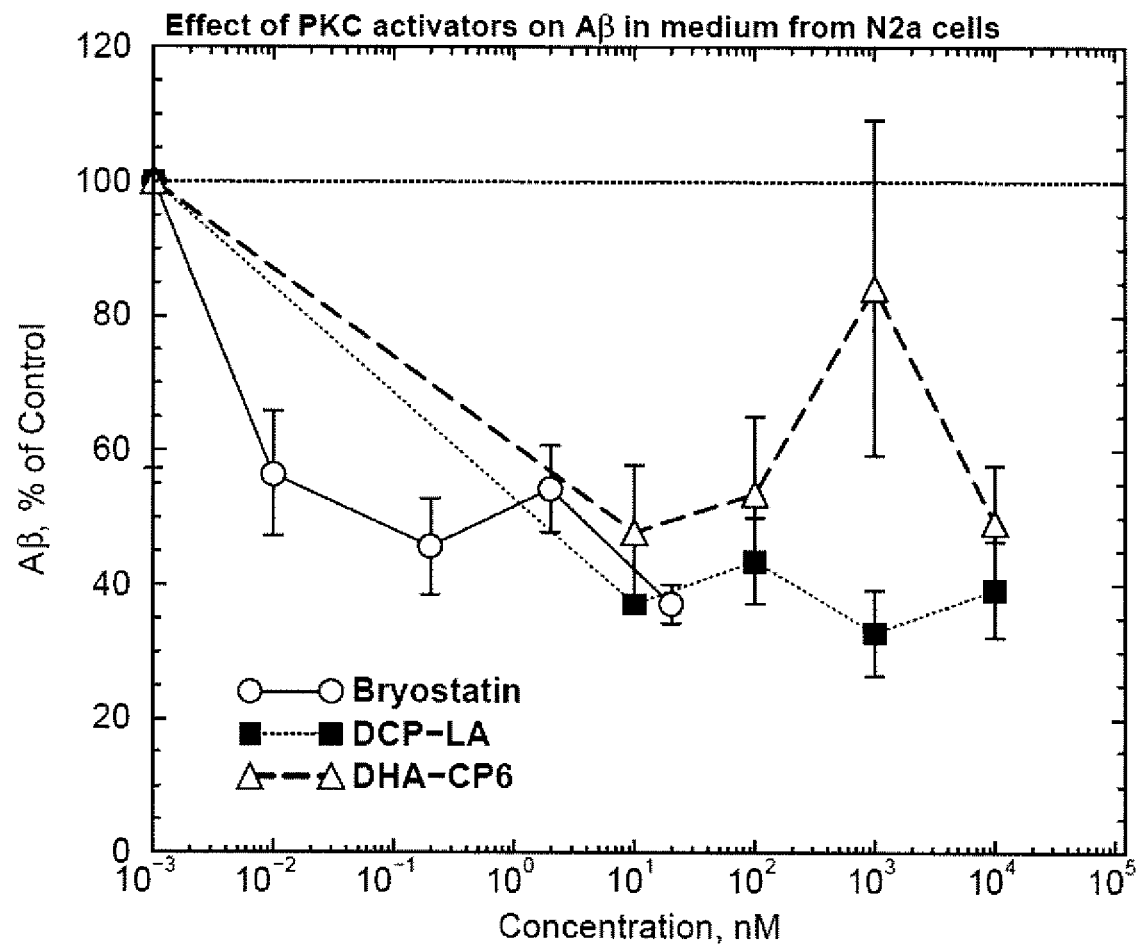

To measure the effects of PKCε activation on Aβ production, we used mouse neuro2a (N2a) neuroblastoma cells transfected with human APPSwe/PSID, which produce large quantities of Aβ. Petanceska et al., *J. Neurochem.* 1996; 74: 1878-84. Incubation of these cells for 24 h with various concentrations of PKC activators, bryostatin, BR-101 (DCP-LA) and BR-111 (DHA-CP6) markedly reduced the levels of both intracellular (FIG. 7a) and secreted (FIG. 7b) Aβ. With bryostatin, which activates PKC by binding to the diacylglycerol-binding site, the inhibition was biphasic, with concentrations of 20 nM or higher producing no net effect. This may be explained by the ability of this class of PKC activators to downregulate PKC when used at high concentrations. In contrast, BR-101 (DCP-LA) and BR-111 (DHA-CP6), which bind to PKC's phosphatidylserine site, showed monotonically increasing inhibition at concentrations up to 10 to 100 µM with no evidence of downregulation at higher concentrations.

Figure 8:
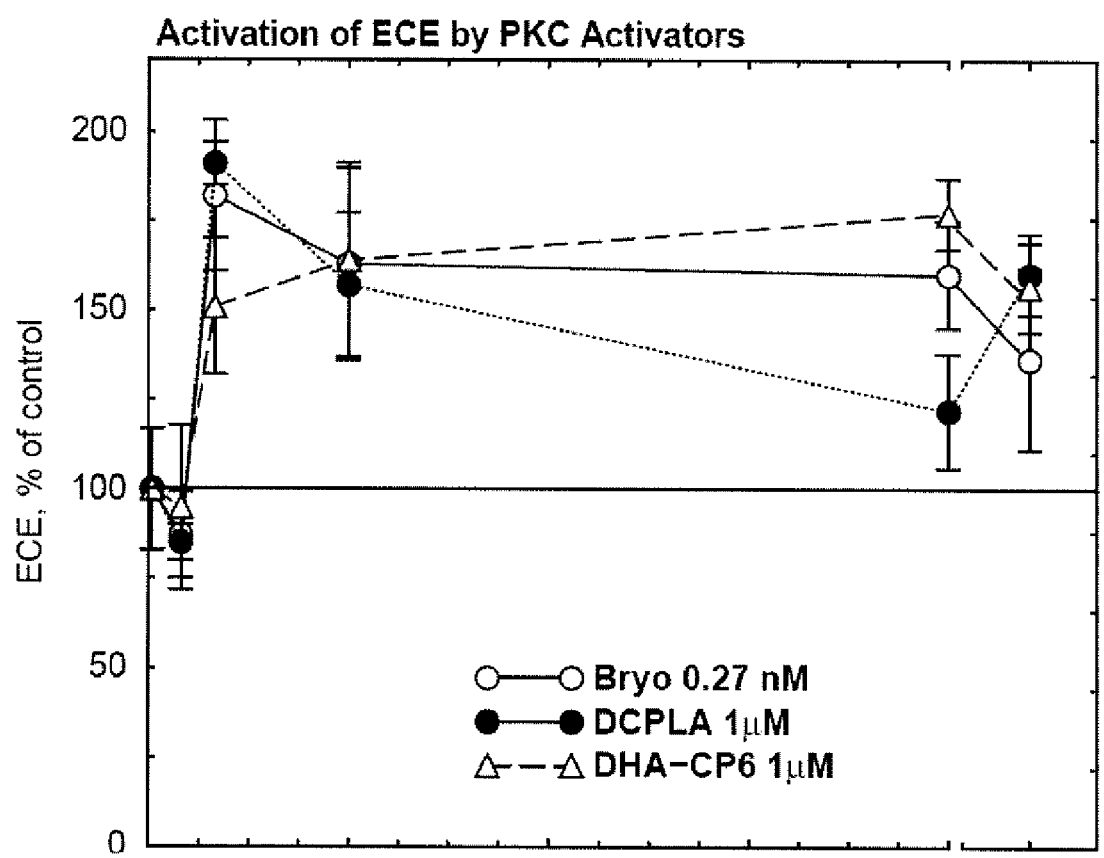
FIG. 8 shows the effect of BR-111 (DHA-CP6) (0.1 to 10 μM) on degradation of exogenously applied Aβ in SH-SY5Y neuroblastoma cells.

To determine whether the reduced levels of Aβ caused by PKC activators were due to inhibition of Aβ synthesis or activation of Aβ degradation, we applied BR-111 (DHA-CP6) (0.01 to 10 µM) and low concentrations (100 nM) of exogenous monomeric Aβ-42 to cultured SH-SY5Y cells. This concentration of Aβ is too low to produce measurable toxicity or cell death. Since SH-SY5Y cells produce only trace amounts of Aβ, this experiment was an effective test of the ability of PKC activators to enhance Aβ degradation. By 24 h, most of the Aβ had been taken up by the cells and the concentration of Aβ in the culture medium was undetectable. Addition of 0.01 to 10 µM DHA-CP6 to the cells reduced the cellular levels of Aβ by 45-63%, indicating that the PKCε activator increased the rate of degradation of exogenous Aβ (FIG. 8).

Figure 11:
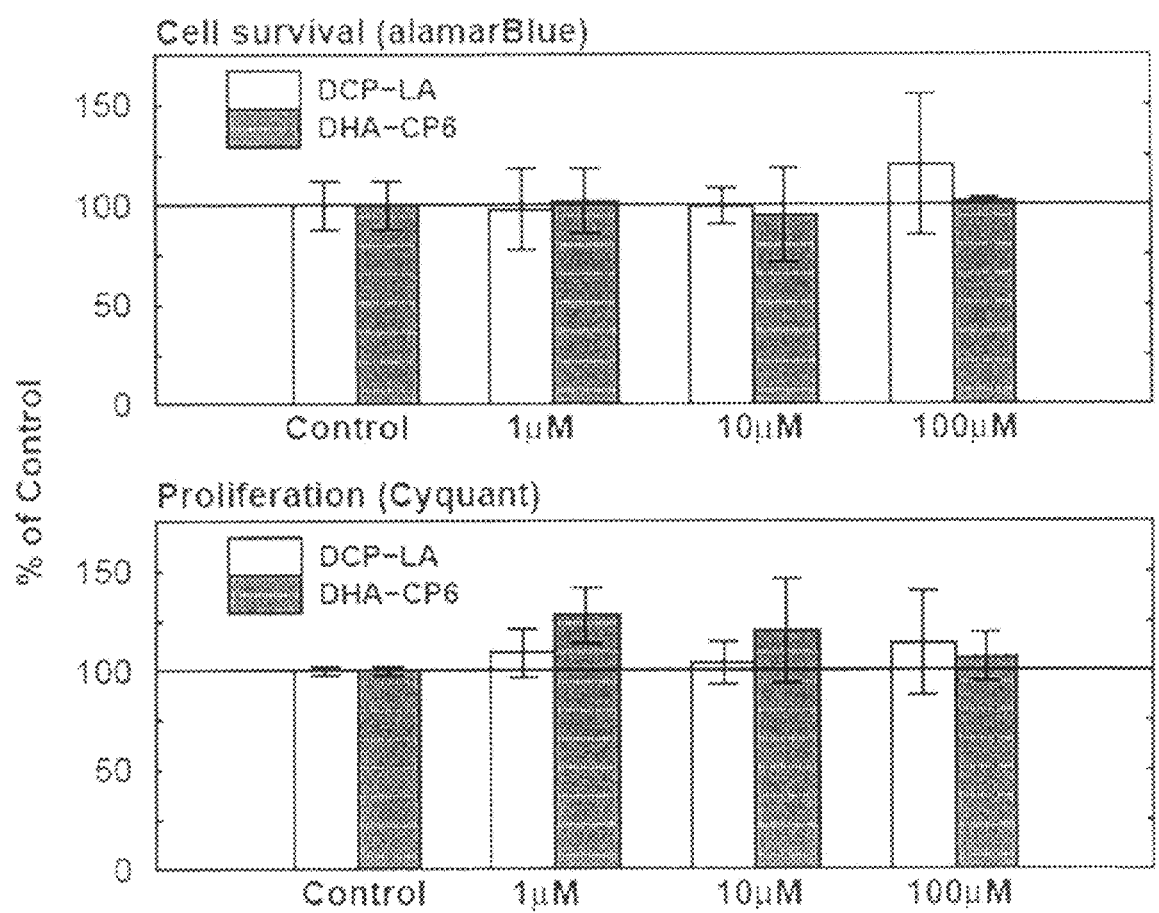
FIGS. 11a-b depict the effect of BR-101 (DCP-LA) and BR-111 (DHA-CP6) (1-100 μM) on cell survival and cell proliferation, respectively, of SH-SY5Y neuroblastoma cells.

DHA-CP6, bryostatin, and DCP-LA had no effect on cell survival or on proliferation as measured by alamar Blue and CyQuant staining (FIGS. 11a and b), indicating that the reduction in Aβ production did not result from cell proliferation or a change in cell survival.

Example 5

Effects of PKC Activators on TACE Activity

TACE Assay. TACE was measured by incubating 5 µl cell homogenate, 3 µl buffer (50 mM Tris-HCl 7.4 plus 25 mM NaCl plus 4% glycerol), and 1 µl of 100 µM TACE substrate IV (Aβz-LAQAVRSSSR-DPa) (Calbiochem) for 20 min at 37° in 1.5-ml polypropylene centrifuge tubes (Jin et al., *Anal. Biochem.* 2002; 302: 269-75). The reaction was stopped by cooling to 4° C. The samples were diluted to 1 ml and the fluorescence was rapidly measured (ex=320 nm, em=420 nm) in a Spex Fluorolog 2 spectrofluorometer.

Results and Discussion

Figure 9:
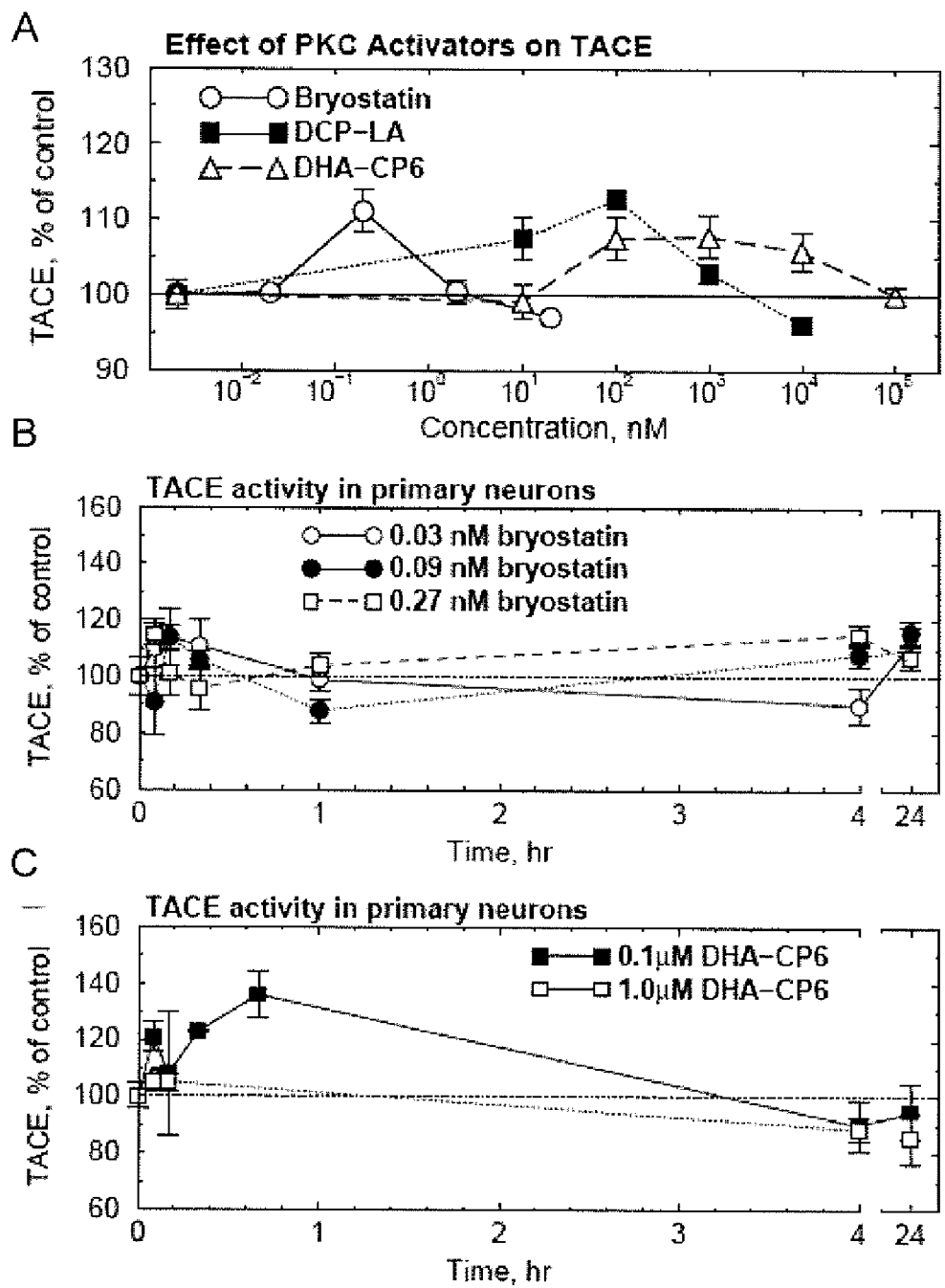
FIGS. 9a-c depict effects of PKC activators PKC activators bryostatin, BR-101 (DCP-LA), and BR-111 (DHA-CP6) on TACE activity in N2a neuroblastoma cells transfected with human APPSwe/PS1D (9a); the effects of various concentrations of bryostatin on TACE activity in rat cortical primary neurons (9b) and the effects of BR-111 (DHA-CP6) on TACE activity in rat cortical primary neurons (9c).

Previous researchers reported that PKC activators such as phorbol 12-myristate 13-acetate produce large increases in TACE activity which correlated with increased sAPPα and decreased Aβ, suggesting that TACE and BACE1 compete for availability of APP substrate, and that PKC activators shift the competition in favor of TACE. Buxbaum et al., *J. Biol. Chem.* 1998; 273: 27765-67; Etcheberrigaray et al., *Proc. Natl. Acad. Sci. USA.* 2006: 103:8215-20. However, many of these earlier studies were carried out in fibroblasts and other non-neuronal cell types, which appear to respond differently to PKC activators than neurons. For example, Etcheberrigaray et al. found that activation of PKC in human fibroblasts by 10 pM to 100 pM bryostatin increased the initial rate of α-secretase activity by 16-fold and 132-fold, respectively (Etcheberrigaray et al., *Proc. Natl. Acad. Sci. USA.* 2006). However, in human SH-SY5Y neuroblastoma cells, N2a mouse neuroblastoma cells (FIG. 9a), and primary neurons from rat hippocampus (FIGS. 9b, c), PKC activators bryostatin, BR-101 (DCP-LA) and/or BR-111 (DHA-CP6) only produced small increases in TACE activity. This suggests that any reduction of Aβ levels in neurons by PKC activators must be caused by some other mechanism besides activation of TACE.

Example 6

Effects of PKC Activators on Endothelin-Converting Enzyme Activity

ECE assay. SH-S757 neuroblastoma cells were incubated with bryostatin (0.27 nM), BR-101 (DCP-LA) (1 µM), and BR-111 (DHA-CP6) (1 µM). Endothelin-converting enzyme (ECE) was measured fluorimetrically using the method of Johnson and Ahn, *Anal. Biochem.* 2000; 286: 112-118. A sample of cell homogenate (20 µl) was incubated in 50 mM MES-KOH, pH 6.0, 0.01% C12E10 (polyoxyethylene-10-lauryl ether), and 15 µM McaBK2 (7-Methoxycoumarin-4-acetyl [Ala7-(2,4-Dinitrophenyl)Lys9]-bradykinin trifluoroacetate salt) (Sigma-Aldrich). After 60 min at 37° C., the reaction was quenched by adding trifluoroacetic acid to 0.5%. The sample was diluted to 1.4 ml with water and the fluorescence was measured at ex=334 nm, em=398 nm.

Results and Discussion

Figure 10:
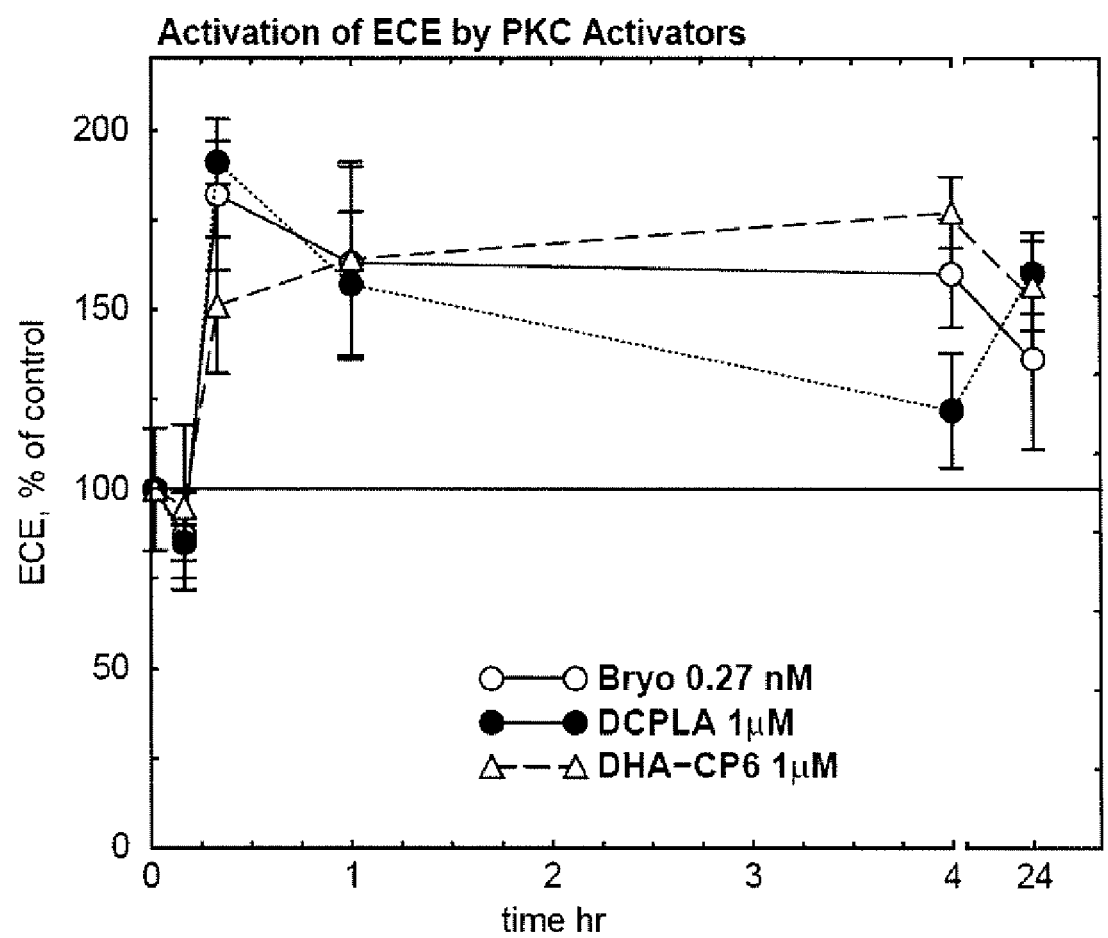
FIG. 10 shows the activation of endothelin converting enzyme (ECE) by PKC activators bryostatin (0.27 nM), BR-101 (DCP-LA) (1 μM), BR-111 (DHA-CP6) (1 μM), or ethanol in SU-SY5Y neuroblastoma cells.

Aβ can be degraded in vivo by a number of enzymes, including insulin degrading enzyme (insulysin), neprilysin, and ECE. Because PKCε overexpression has been reported to activate ECE (Choi et al., *Proc. Natl. Acad. Sci. USA.* 2006; 103: 8215-20), we examined the effect of PKC activators on ECE. Bryostatin, BR-101 (DCP-LA), and BR-111 (DHA-CP6) all produced a sustained increase in ECE activity (FIG. 10). Since ECE does not possess a diacylglycerol-binding C1 domain, this suggests that the activation by bryostatin was not due to direct activation of ECE, but must have resulted from phosphorylation of ECE or some ECE-activating intermediate by PKC. This result also suggests that indirect activation ECE by PKC activators could be a useful means of reducing the levels of Aβ in patients.

An advantage of compounds such as the PUFA derivatives of the present invention which specifically activate PKCε is that they produce less down-regulation than phorbol esters and similar 1,2-diacylglycerol (DAG) analogues. The biphasic response of PKC to DAG-based activators means that a PKC activator may reduce Aβ levels at one time point and increase them at another. da Cruz e Silva et al., *J. Neurochem.* 2009; 108: 319-330. Careful dosing and monitoring of patients would be required to avoid effects opposite to those that are intended. Because of the relative inability of this new class of PKC activators to downregulate PKC, this problem can be avoided.

Patents, patent applications, publications, product descriptions, and protocols are cited throughout this application, the disclosures of which are incorporated herein by reference in their entireties for all purposes.

What is claimed:

1. A method of activating an epsilon isoform of protein kinase C comprising contacting the epsilon isoform of protein kinase C with an effective amount of at least one compound chosen from a cis-polyunsaturated fatty acid ester in which at least one of the double bonds is replaced by a cyclopropyl group.

2. The method of claim 1, wherein all of the double bonds are replaced by cyclopropyl groups.

3. The method of claim 1, wherein the fatty acid from which the compound is derived has a structure of

or

wherein X is between 2 and 6 and Y is between 2 and 6.

4. The method of claim 1, wherein the polyunsaturated fatty acid from which the compound is derived is chosen from arachidonic acid, docosapentaenoic acid, docosahexaenoic acid, eicosapentaenoic acid, linoleic acid, γ-linoleic acid, α-linolenic acid, eicosatetraenoic acid, adrenic acid, and derivatives thereof.

5. The method of claim 1, wherein the compound is chosen from cyclopropanated docosahexaenoic acid methyl ester (BR-111), cyclopropanated eicosapentaenoic acid methyl ester (BR-114), and cyclopropanated arachidonic acid methyl ester (BR-115).

6. The method of claim 1, wherein the ester is a fatty acid alcohol ester.

7. The method of claim 6, wherein the alcohol is an aliphatic alcohol.

8. The method of claim 7, wherein the aliphatic alcohol is glycerol.

9. The method of claim 1, wherein the effective amount of the compound is between about 5 nanomolar to about 10 micromolar.

10. The method of claim 1,
wherein the compound activates the epsilon isoform of protein kinase C at least 2-fold over the alpha isoform of protein kinase C or over an epsilon isoform of protein kinase C not contacted with the compound.

11. A method for reducing neurodegeneration comprising administering to a subject in need thereof an effective amount of at least one compound chosen from a cis-polyunsaturated fatty acid ester in which at least one of the double bonds is replaced by a cyclopropyl group.

12. The method of claim 11, wherein all of the double bonds are replaced by cyclopropyl groups.

13. The method of claim 11, wherein the fatty acid from which the compound is derived has a structure of

or

wherein X is between 2 and 6 and Y is between 2 and 6.

14. The method of claim 11, wherein the polyunsaturated fatty acid from which the compound is derived is chosen from arachidonic acid, docosapentaenoic acid, docosahexaenoic acid, eicosapentaenoic acid, linoleic acid, γ-linoleic acid, α-linolenic acid, eicosatetraenoic acid, adrenic acid, and derivatives thereof.

15. The method of claim 11, wherein the compound is chosen from cyclopropanated docosahexaenoicacid methyl ester (BR-111), cyclopropanated eicosapentaenoic acid methyl ester (BR-114), and cyclopropanated arachidonic acid methyl ester (BR-115).

* * * * *

UNITED STATES PATENT AND TRADEMARK OFFICE
CERTIFICATE OF CORRECTION

| | | |
|---|---|---|
| PATENT NO. | : 8,163,800 B2 | Page 1 of 1 |
| APPLICATION NO. | : 12/510681 | |
| DATED | : April 24, 2012 | |
| INVENTOR(S) | : Thomas J. Nelson et al. | |

It is certified that error appears in the above-identified patent and that said Letters Patent is hereby corrected as shown below:

Title page, item 57, line 1, "methods of activate" should read --methods of activating--.

Signed and Sealed this
Thirty-first Day of July, 2012

David J. Kappos
*Director of the United States Patent and Trademark Office*